United States Patent
Zandi et al.

(10) Patent No.: US 12,029,635 B2
(45) Date of Patent: Jul. 9, 2024

(54) CATHETER-BASED APPARATUSES AND METHODS WITH FILTER POUCH

(71) Applicant: Transverse Medical, Inc., Evergreen, CO (US)

(72) Inventors: Abdolrahim Zandi, Laguna Niguel, CA (US); J. Eric Goslau, Evergreen, CO (US)

(73) Assignee: Transverse Medical, Inc., Evergreen, CO (US)

( * ) Notice: Subject to any disclaimer, the term of this patent is extended or adjusted under 35 U.S.C. 154(b) by 86 days.

(21) Appl. No.: 17/761,438

(22) PCT Filed: Sep. 18, 2020

(86) PCT No.: PCT/US2020/051582
§ 371 (c)(1),
(2) Date: Mar. 17, 2022

(87) PCT Pub. No.: WO2021/055810
PCT Pub. Date: Mar. 25, 2021

(65) Prior Publication Data
US 2022/0346932 A1 Nov. 3, 2022

Related U.S. Application Data

(60) Provisional application No. 62/902,742, filed on Sep. 19, 2019.

(51) Int. Cl.
*A61F 2/01* (2006.01)
(52) U.S. Cl.
CPC ............ *A61F 2/012* (2020.05); *A61F 2/0108* (2020.05); *A61F 2002/016* (2013.01); *A61F 2002/018* (2013.01)

(58) Field of Classification Search
CPC .... A61F 2/01; A61F 2230/0008; A61F 2/011; A61F 2/012; A61F 2/0108;
(Continued)

(56) References Cited

U.S. PATENT DOCUMENTS

2014/0031857 A1   1/2014 Richardson
2017/0143356 A1*  5/2017 Zandi ................... A61B 17/221
(Continued)

FOREIGN PATENT DOCUMENTS

WO   1998/049952 A1   11/1998
WO   2017/042808 A1   3/2017
(Continued)

OTHER PUBLICATIONS

ISA/EPO (The Hague), EP20865232.1, Extended European Search Report mailed Oct. 13, 2022, Melanie Geuer (7 pgs).
(Continued)

*Primary Examiner* — Sarah A Long
*Assistant Examiner* — James R McGinnity
(74) *Attorney, Agent, or Firm* — Crawford Maunu PLLC

(57) ABSTRACT

As may be implemented in accordance with one or more embodiments characterized herein, aspects of the present disclosure are directed to an apparatus including first and second filters, a shaft and a frame coupled to the shaft and to the first filter. The frame and shaft operate to seal a perimeter of the first filter around an opening in a sidewall of a tubular structure, by pressing the frame against the perimeter and the sidewall. The second filter is also coupled to the frame and operates with the frame to extend into cross section of the tubular structure away from the frame and the sidewall, with the frame sealing the first filter around the opening, and to filter particles from fluid flowing past the opening and along the length of the sidewall.

23 Claims, 17 Drawing Sheets

(58) Field of Classification Search
CPC .......... A61F 2002/016; A61F 2002/018; A61F 2/0105; A61F 2230/0069; A61F 2/00; A61F 2250/0069; A61B 2017/0225
See application file for complete search history.

(56) References Cited

U.S. PATENT DOCUMENTS

| | | | |
|---|---|---|---|
| 2017/0172591 A1* | 6/2017 | Ulm, III | B23K 26/40 |
| 2019/0000604 A1 | 1/2019 | Eli | |
| 2019/0060051 A1 | 2/2019 | Scheeff et al. | |
| 2019/0201191 A1* | 7/2019 | McLean | A61F 2/0063 |

FOREIGN PATENT DOCUMENTS

| | | |
|---|---|---|
| WO | 2018/183321 A1 | 10/2018 |
| WO | 2019/173475 A1 | 9/2019 |

OTHER PUBLICATIONS

ISA/US, PCT/US20/51582, PCT Search Report and Written Opinion mailed Jan. 5, 2021, Shane Thomas (11 pgs).

\* cited by examiner

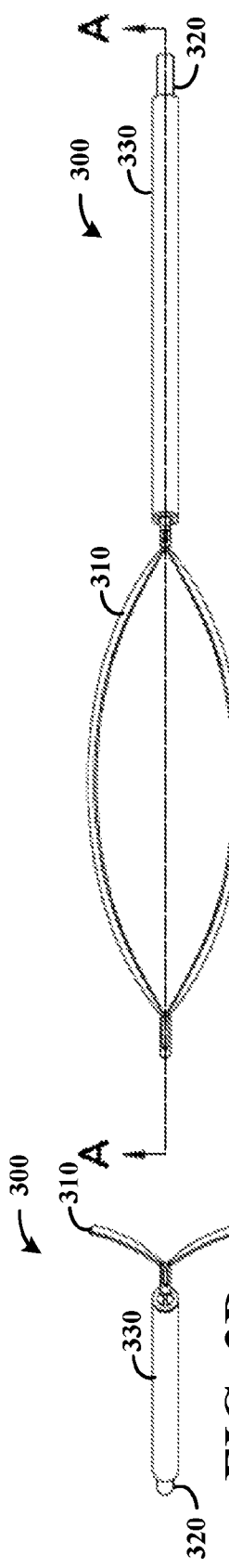
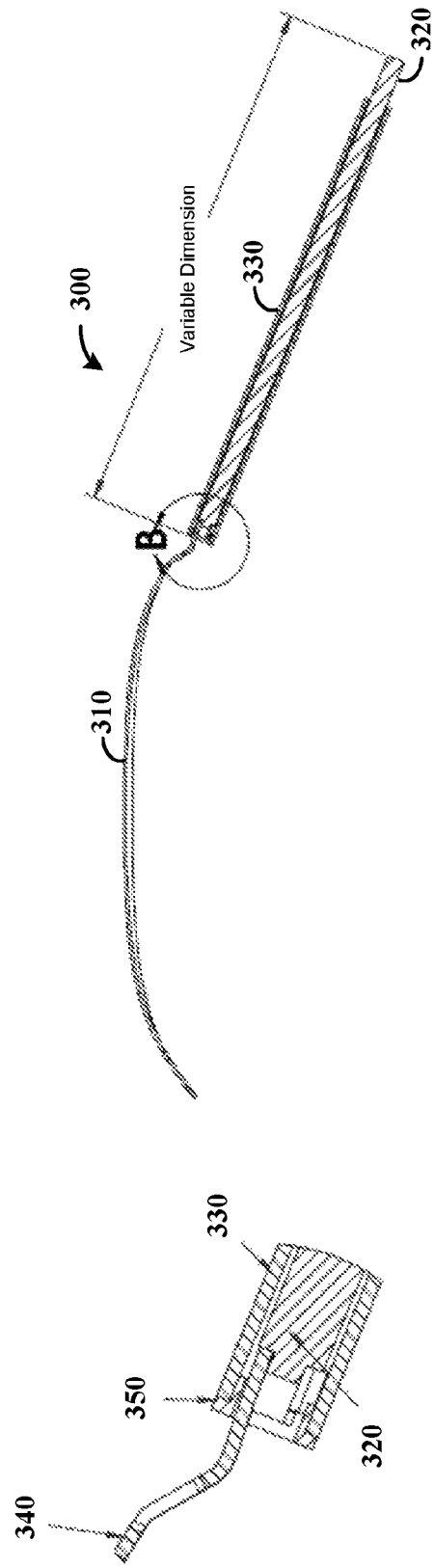
FIG. 3A
FIG. 3B SECTION A-A
FIG. 3C DETAIL B
FIG. 3D

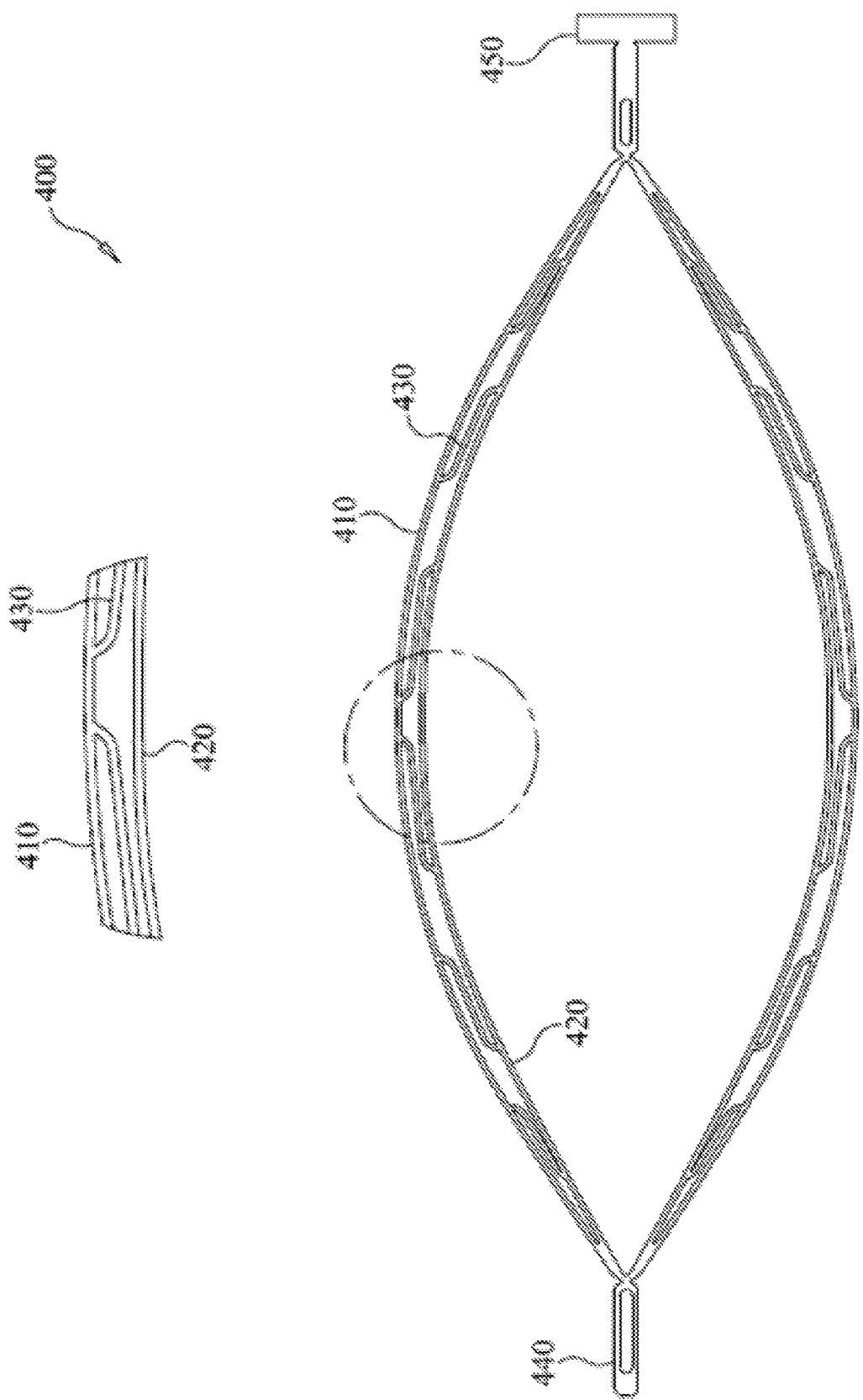

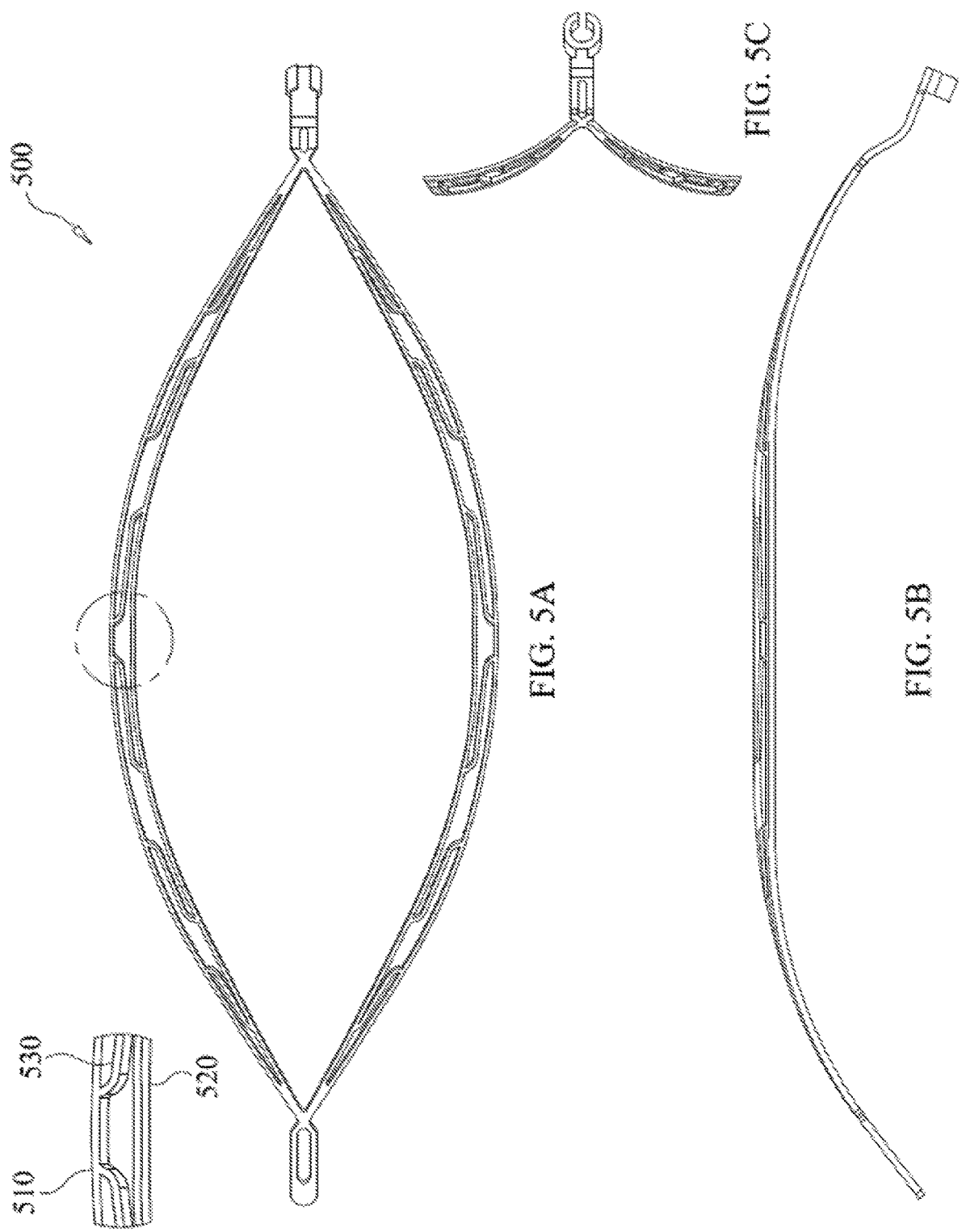

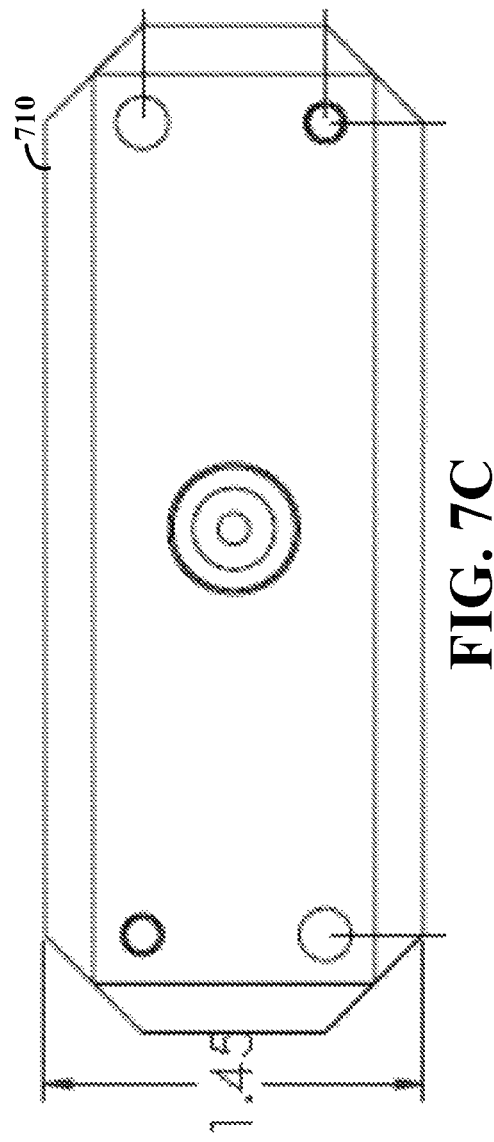
FIG. 7C
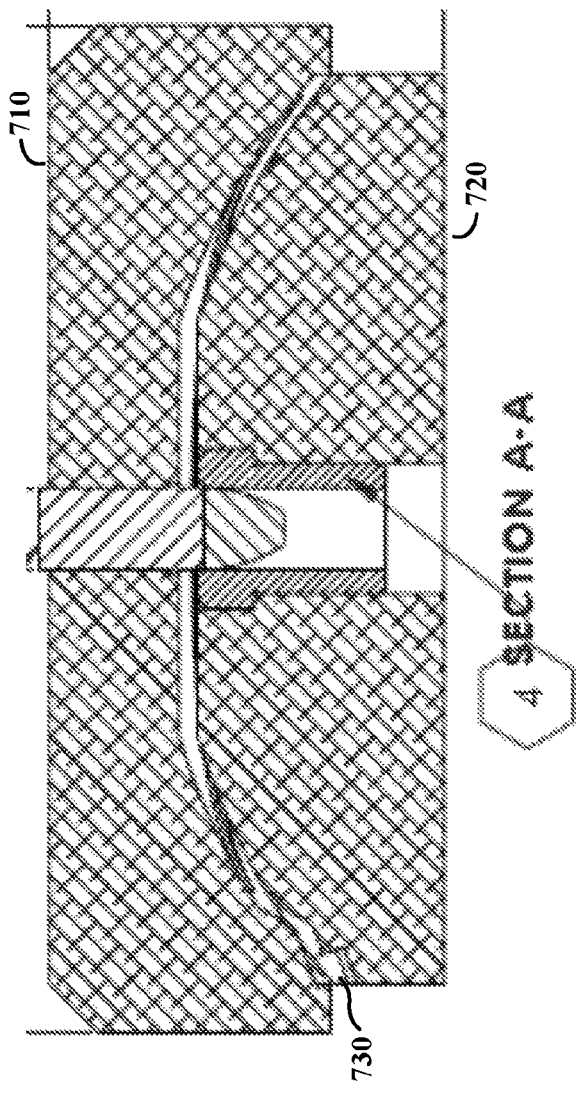
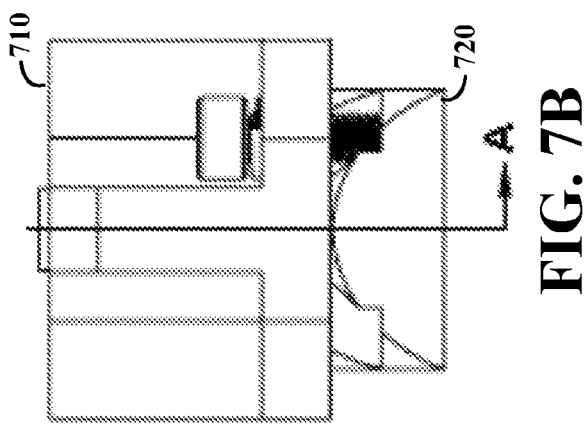
FIG. 7B

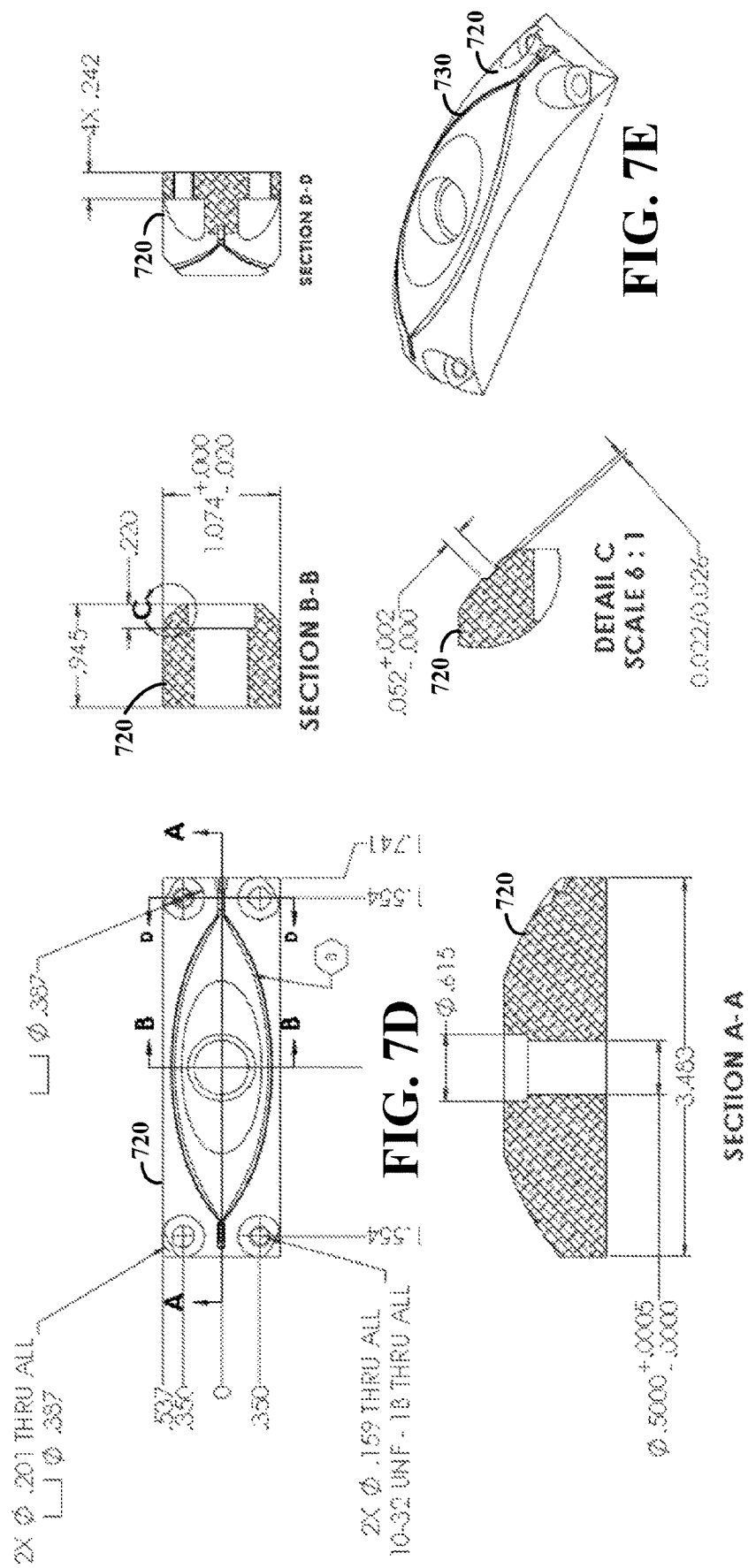

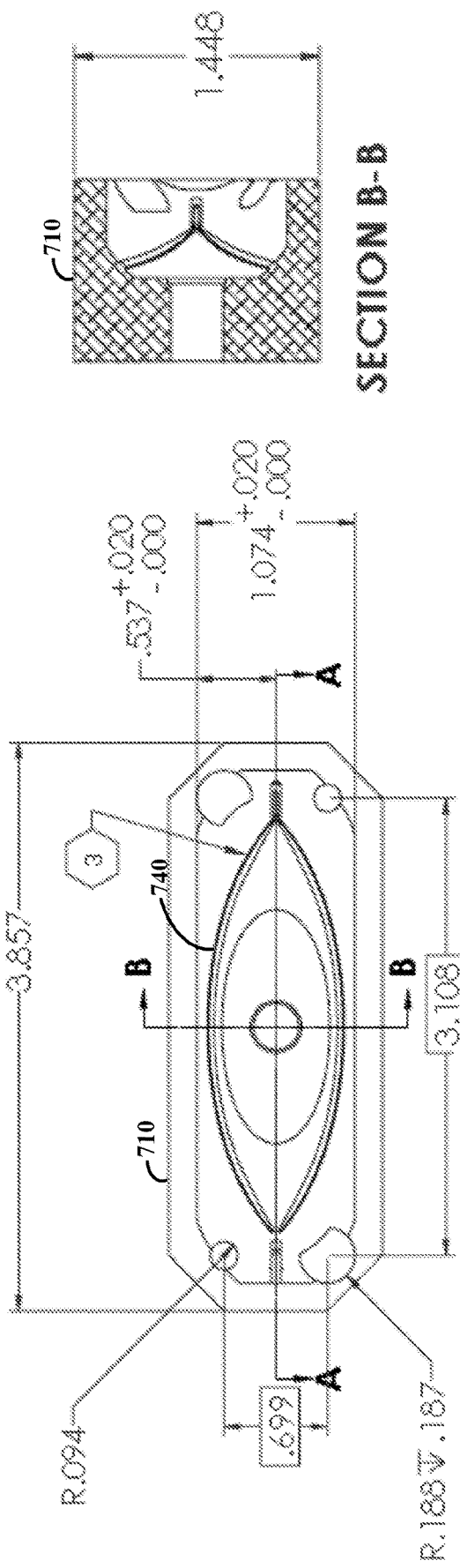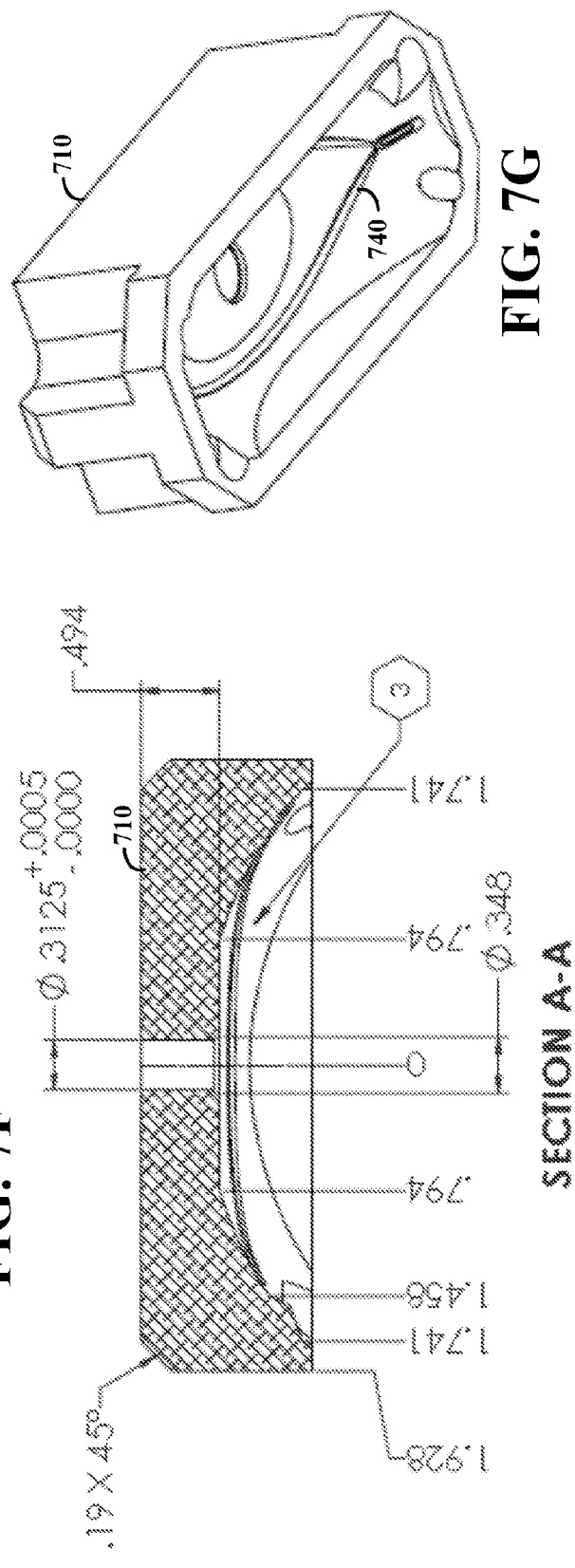
FIG. 7F
FIG. 7G

CATHETER-BASED APPARATUSES AND METHODS WITH FILTER POUCH

OVERVIEW

Particulates may pass through pipes or other channels in a variety of different applications. It may be desirable to filter such particulates, such as to remove the particulates from fluid and/or to prevent flow of the particulates in a particular channel, for instance such as a side channel branching off of a main channel. For instance, it may be useful to filter fluid flowing through tubing in a manufacturing setting, for automotive, medical and other applications.

One particular application in which filtering may be useful includes the treatment of medical conditions, such as coronary heart disease, aneurism and others. These treatments can often involve intervention with tissue, such as to remove, repair or otherwise treat tissue. For instance, coronary heart disease can sometimes involve heart valve disorders, which can be addressed via intervention techniques in which valves are repaired or replaced.

One manner that has been useful for treating various conditions involves the use of a catheter to enter a patient's arteries and provide access for a variety of techniques. For instance, various procedures can be performed via catheters, such as to repair or remove tissue, or to implant tissue or other devices. One such approach for addressing heart disease involves transcatheter-aortic valve replacement or implementation therapies (TAVR/TAVI). These and other trans-vascular approaches may involve the delivery of artificial or animal flaps/valves to a patient's heart via catheters.

While many treatment approaches have been useful, there have been many challenges to their safe implementation. It is common to introduce, cross and exchange a variety of percutaneous devices such as guide wires, catheters, sheaths, guide catheters, and adjunctive technologies to gain access to and treat a coronary vessel, coronary valve, or other vascular anatomy. These and other approaches to the repair or replacement of tissue can dislodge particles/debris (emboli) which are freed (released) from the vessel walls and structures causing uncontrolled and unprotected floating emboli to move freely. This freed emboli, and freely floating and uncontrolled emboli can be carried distally (away) via the blood stream and cause issues, such as by blocking or occluding coronary, peripheral, and neurovascular vessels. For instance, during the (TAVR/TAVI) procedure, native tissue can be compressed into the aorta wall to make room for replacement devices. This action may cause dislodging or displacement of arterial plaque, calcium, or thrombus as the devices transverse the aortic arch. These particles can have adverse effects, such as by causing a stroke. These and other matters have presented challenges to a variety of treatment approaches.

Various example embodiments are directed to catheter-based apparatuses and their implementation. In connection with one or more such embodiments, a pouch type filter is utilized with a catheter, for filtering material flowing within a tubular structure. Such a pouch-type filter may be coupled with other catheter componentry, such as another filter, tools for performing operations, fluid delivery components, and more.

According to another example embodiment, a catheter-type apparatus includes a filter component having a frame connected to a shaft. A sheet-type filter material is coupled to the frame for expansion and coverage of one or more openings in a sidewall of a tubular structure, and a pouch-type filter material is coupled to the frame and/or shaft. The frame and shaft are configured to position/conform the frame and sheet-type filter to the sidewall for filtering material flowing into or out of the one or more openings, and the pouch-type filter is configured to extend into tubular structure for filtering material flowing within the tubular structure.

In various embodiments, the aforementioned catheter-type apparatus is configured for use in an aortic arch, with the shaft, frame and both the sheet-type and pouch-type filter material delivered via an outer catheter. In a particular use-case scenario, the shaft operates to extend the frame and both filters into the aortic arch, to conform the frame to sidewall openings therein (e.g., over vessels leading away from the aortic arch for delivering blood accordingly), and generally sealing the sheet-type filter material around the sidewall openings. The pouch-type filter material is then extended (actively or by way of its configuration) into the upper aortic arch. This operates to filter blood passing out of the aortic arch via the sidewall openings, and to filter blood flowing in the aortic arch itself. Further, this approach permits the passage of an additional catheter through the upper aortic arch while the sidewall openings are sealed. This can be useful, for example, during heart valve procedures such as discussed herein, and may address related issues as noted above.

In various embodiments, a catheter-based apparatus and approach is implemented to mitigate undesirable fluid flow characteristics, such as turbulence, eddy currents and vortices that may form around components of the catheter or the catheter itself as deployed in a tubular structure. In certain implementations, laminar flow is generated by utilizing components of a catheter apparatus coupled to a filter or other structure fur interacting with fluid flowing in a tubular vessel in which the catheter apparatus is deployed. Certain implementations involve utilizing a filter as characterized herein, with control of fluid flowing around or adjacent the filter to mitigate such effects. For instance, a pouch-type filter can be used to facilitate one of more of: reacting to flow variation, reduce high angles of attack relative to a sheet-type filter secured around sidewall openings, reduce a pressure gradient along such a sheet-type filter or other component, collect large larger size emboli (e.g., to preventing them from collecting via aft flow). Such a pouch-type filter can further mitigate the creation of turbulence, eddy currents and/or vortices.

The following embodiments may further exemplify applications in which a pouch and/or fluid flow control may be implemented.

According to another example embodiment, an apparatus includes a catheter extending from a proximal end to a distal end, a shaft within and operable to move in the catheter, and a filter component that is connected to the shaft and operable to retract within the distal end of the catheter. The filter component includes a mesh and inner and outer frames connected by struts. A perimeter of the mesh is coupled to the inner frame (and in some instances, to the outer frame), with the inner and outer frame extending along one another. The struts operate to apply a force between the outer frame and the inner frame, such as by applying a force that applies the inner frame and mesh against tissue (e.g., within vascular tissue).

Another embodiment is directed to a method as follows. A filter component is deployed from within a catheter, in which the filter component has inner and outer frames coupled by struts with a mesh coupled to a perimeter of the inner frame. The filter component is deployed by manipulating a shaft that extends from a proximal end of the catheter toward a distal end of the catheter, with the filter component coupled to a distal end of the shaft. A force that seals the mesh to an inner tissue wall is applied by manipulating the shaft and using the outer frame and struts to direct the force against the inner frame and the mesh.

In various implementations, the catheter is inserted into a human aortic arch and the filter component is deployed over at least one artery opening in the aortic arch. The mesh is sealed to a portion of an inner wall of the aortic arch around the at least one artery opening, and used to capture particles in blood flowing into the at least one artery opening. In further implementations, the mesh, frames and struts are collapsed with the captured particles therein, and the mesh, frames, struts and particles are retracted into the catheter that can then be removed.

The above discussion/summary is not intended to describe each embodiment or every implementation of the present disclosure. The figures and detailed description that follow also exemplify various embodiments.

DESCRIPTION OF THE FIGURES

Various example embodiments may be more completely understood in consideration of the following detailed description in connection with the accompanying drawings, in which:

FIGS. 3A-3D show respective views of a catheter apparatus, in accordance with one or more example embodiments of the present disclosure;

FIG. 4 shows a filter support apparatus, in accordance with one or more example embodiments of the present disclosure;

FIGS. 5A-5C show respective views of a filter support apparatus, in accordance with one or more example embodiments of the present disclosure;

FIGS. 7A-7G show respective views of a filter support manufacturing apparatus, in accordance with one or more example embodiments of the present disclosure;

Figure 1:
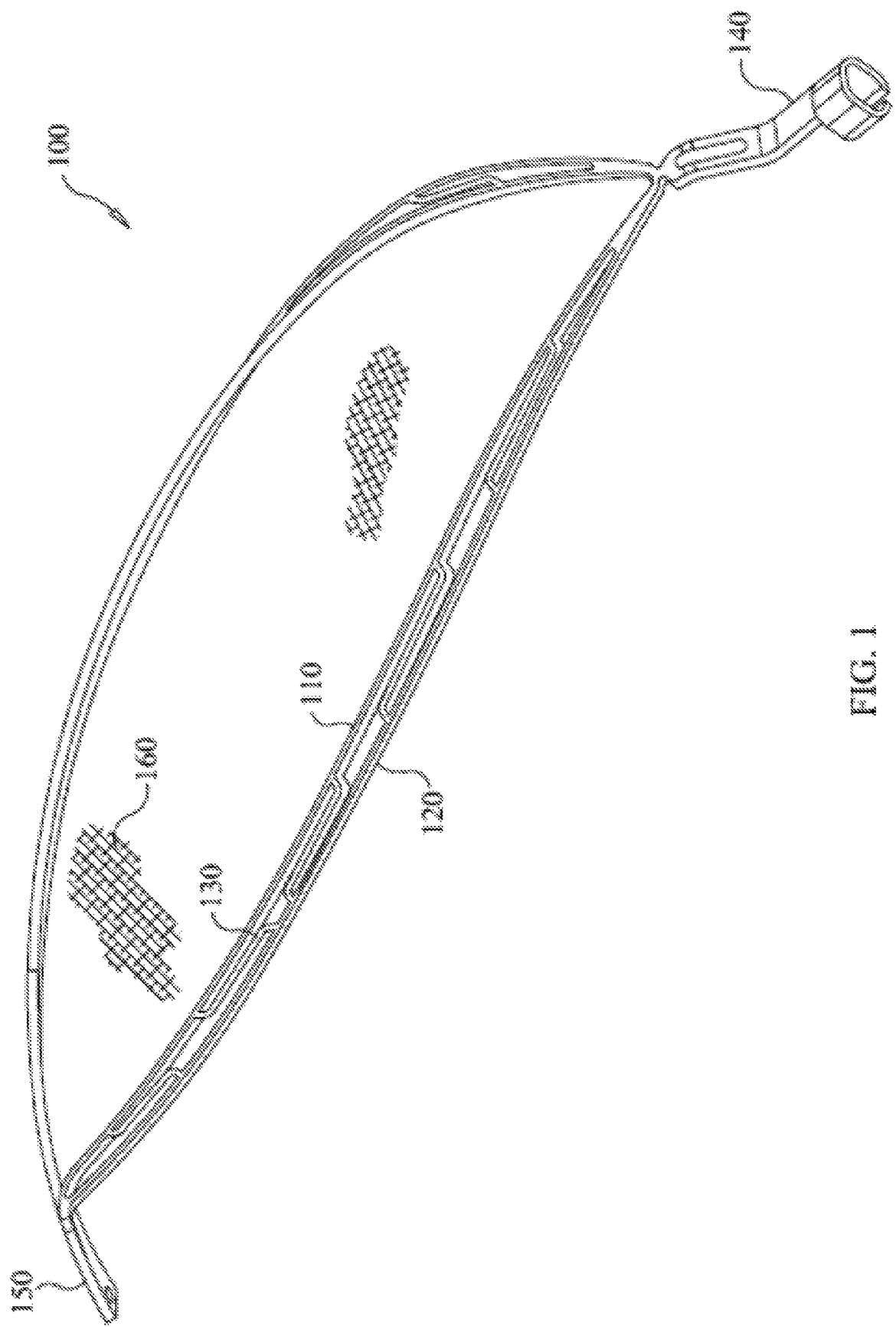
FIG. 1 shows a filter support apparatus, in accordance with one or more example embodiments of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems and methods involving filters, such as filters implemented with catheter-based apparatuses, and related methods. While not necessarily so limited, various aspects may be appreciated through a discussion of examples using this context. For instance, certain embodiments are directed to filtering blood flow into vascular tissue, which can be useful for trapping particulates while allowing the flow of blood. In a particular embodiment, an apparatus includes a filter type membrane that filters particles from blood flow, and which may be deployed using a catheter.

In connection with various embodiments, it has been recognized/discovered that, utilizing a pouch or collective reservoir in accordance with one or more aspects herein may would mitigate the formation of localized eddy currents and large pressure variations across a sealing boundary. In various contexts, features on a filter and related frame may be utilized to guide flow relative to such a pouch or reservoir, which may slow movement of larger debris making the debris more readily captured by the pouch or reservoir. In some instances, such features may push debris toward the pouch or reservoir.

Another embodiment is directed to an apparatus including a first filter, a shaft, and a frame coupled to the shaft and to the first filter. The frame is configured with the shaft to seal a perimeter of the first filter around an opening in a sidewall of a tubular structure, by pressing the frame against the perimeter and the sidewall. The apparatus also includes a second filter coupled to the frame and configured therewith to extend into a cross section of the tubular structure away from the frame and the sidewall, with the frame sealing the first filter around the opening, and to filter particles from fluid flowing past the opening and along the length of the sidewall.

Another embodiment is directed to an apparatus comprising, an extension arm, a frame having a proximal end coupled to the extension arm, a distal end, and respective rails extending between the proximal and distal ends and forming a perimeter of the frame. The apparatus also includes a filter coupled to the perimeter and including opposing inner and outer surfaces of a common portion of filter material terminating at the rails, and a pouch portion having edges connected to a portion of the rails near the proximal end and configured to extend away from the opposing surfaces. The pouch portion is configured and arranged with the inner surface to form a partially enclosed filter bound internally by a portion of the inner surface and the pouch portion. The extension arm is configured with the frame and filter to apply a force to the frame that seals the outer surface of the filter material around an opening in an interior sidewall of a tubular structure to filter fluid exiting the tubular structure via the opening, with the pouch portion extending into the tubular structure for filtering fluid flowing past the frame in the tubular structure.

Figure 10:
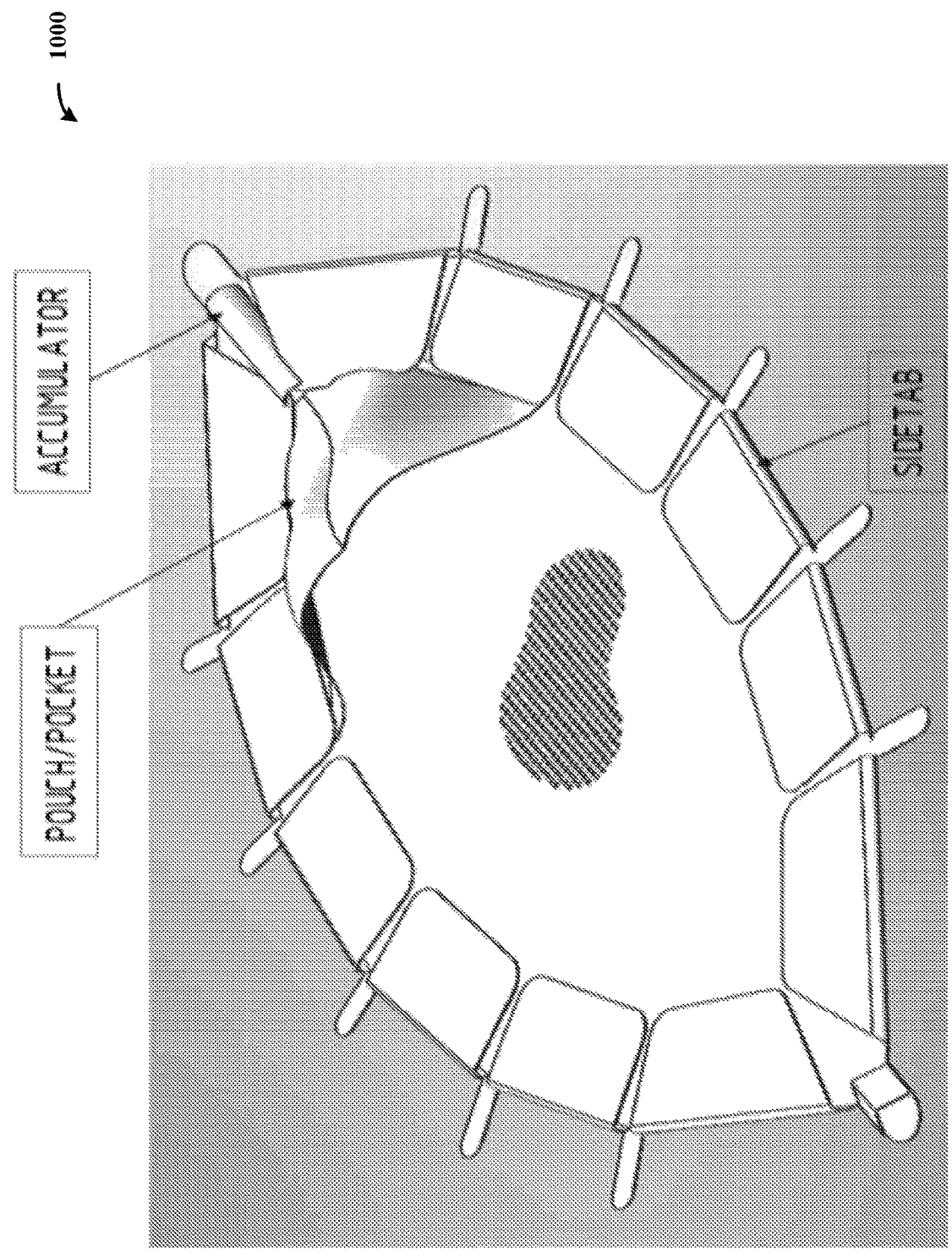
FIG. 10 shows a top view of a filter with a pouch and fins, as well as a frame to which the filter is coupled, in accordance with another embodiment.
Figure 11:
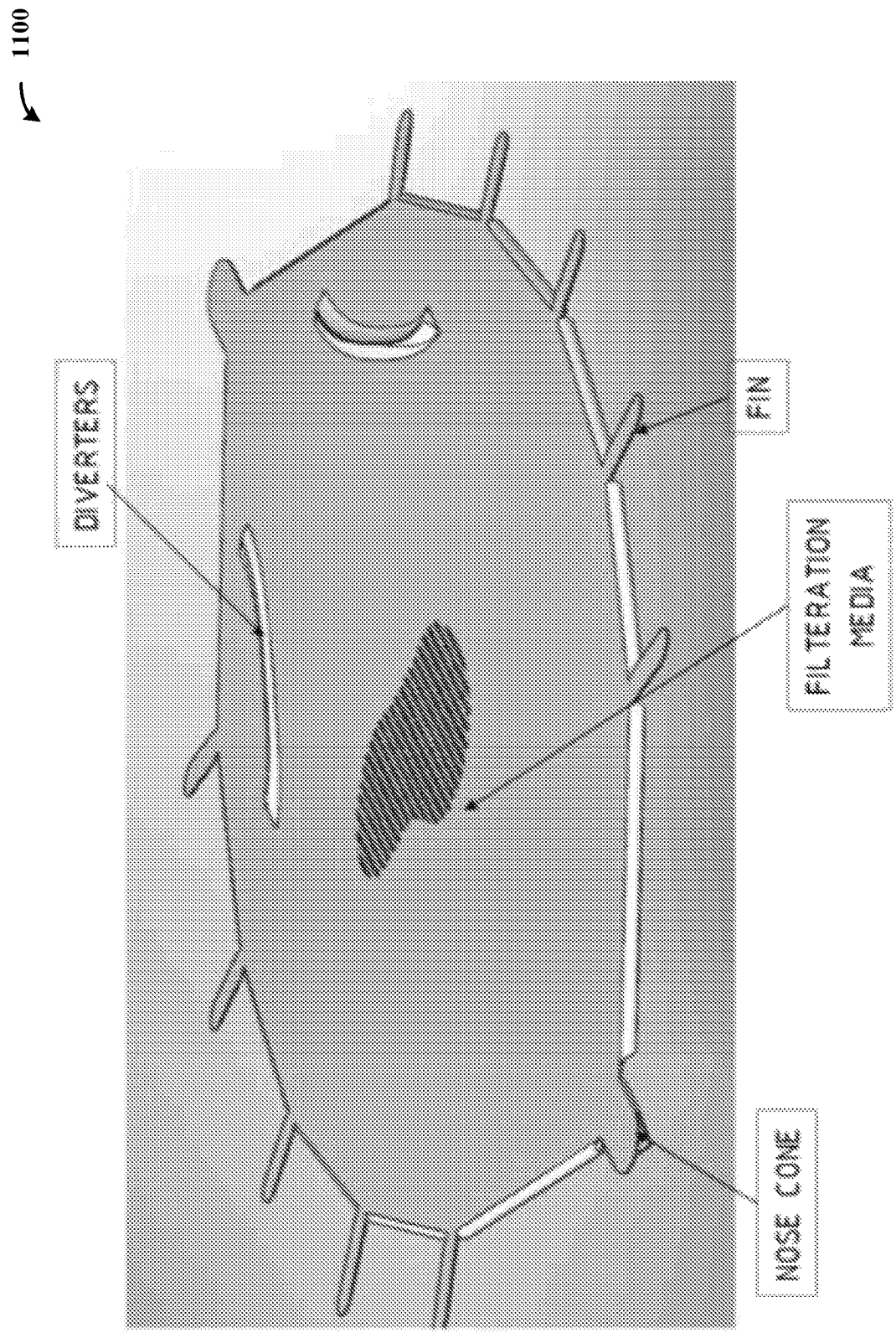
FIG. 11 shows a bottom view of a filter with a pouch and fins, as well as a frame to which the filter is coupled, and which may be implemented in connection with FIG. 10, in accordance with one or more embodiments.

Referring to FIGS. 10 and 11, a pouch/pocket type component of a filter is shown integrated with a filter (e.g., a mesh) and frame as may be implemented in accordance with one or more embodiments herein. The filter is secured to itself and over the frame, resulting in opposing surfaces of the filter on opposing sides of the frame with the surfaces meeting/terminating at the frame. In some implementations, the filter slides freely over the frame, which facilitates movement of the frame within a catheter (or when deployed). An area near an accumulator and nose cone as shown may be attached to proximal and distal portions of the frame. The nose cone may resist pulling and friction force of the filter as the frame/filter assembly is pushed/pulled through a catheter and deployed. Diverters and fins as shown extending from a filter mesh 1100 shown in FIG. 11 may be incorporated to facilitate desirable flow, such as to mitigate eddy currents as characterized herein.

Figure 2:
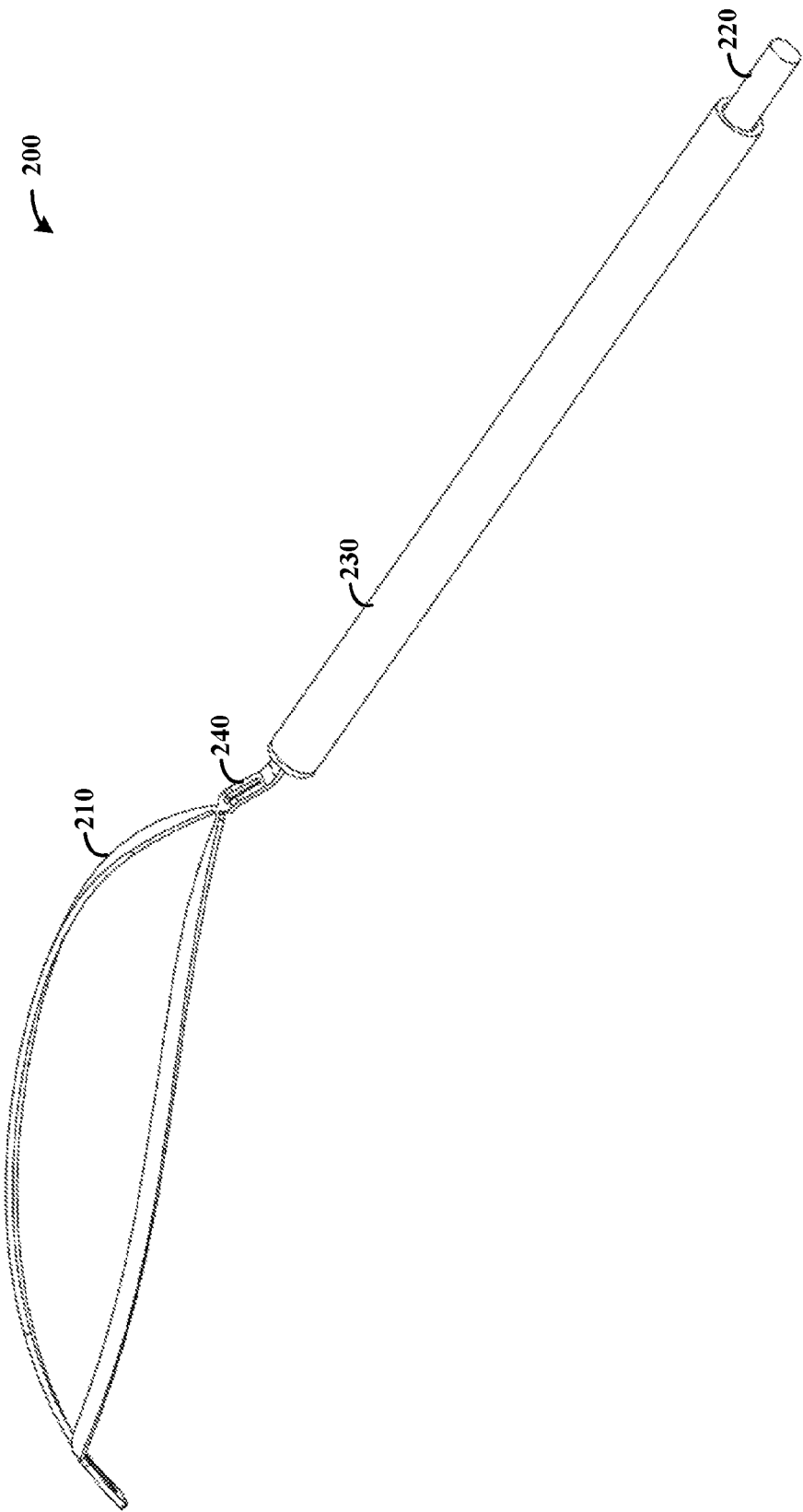
FIG. 2 shows a catheter apparatus, in accordance with one or more example embodiments of the present disclosure.

The filter apparatus 1000 and related approach shown in FIG. 10 may be utilized with a multitude of frames, such as those shown in FIGS. 1 and 2, and with other frames as my employ asymmetrical characteristics. A filter mesh is formed around a frame, with side tabs folding around the frame and secured as shown, with a pouch pocket configured to extend from the mesh for trapping particulates into an accumulator. As may be implemented with various embodiments, a frame such as that shown in FIG. 10 or in the other figures may be utilized to create a sealing force against the upper walls of aortic arch, encapsulating great arteries within a perimeter of the frame. The filter may be used to filter large size emboli (e.g., greater than 105 microns) and provide either a deflection or capturing mechanism away from the great vessels.

Various embodiments, which may relate to the above or other embodiments herein, may utilize one or more filter and/or frame components to facilitate a streamlined hemodynamic flow environment. Table-1 as characterized below describes functionalities and features that may be utilized, separately or in combination of two or more or with other approaches, to facilitate certain embodiments.

around the interface of the filter/frame and aortic arch, reduce the rotation speed and energy of larger sized emboli, direct particles toward a pouch for collection, direct larger emboli through a reservoir, reduce eddy current flow aft the frame, decrease pressure variation across sealing boundaries, increase the natural frequency of a frame/mesh assembly, resist flow and particle reversal during stagnation segment of cardiac pulse, and dampen shock pulse energy of the blood flow that impacts the frame/filter assembly every cycle. Various such features may be used to provide a reinforcing and containing structure to the frame assembly, and may further be used to create a streamlined stable environment that both collects larger and more energetic emboli and redirects them toward zones of interests.

When used in an aortic arch that increases and decreases its diameter for every cardiac cycle, the frame may operate to maintain pressure and/or expand/contract to maintain a seal onto the sidewall of the aortic arch, and around openings therein. Various components as characterized herein (including that above in Table-1 and described therewith) can be used to ensure that a sufficient force is maintained on the frame to maintain sealing. As such, reducing eddy current, vorticity, turbulence and velocity may facilitate maintaining a seal.

As a particular example, fins as characterized herein (e.g., and shown with FIG. 11) may be used to slow down larger diameter emboli and redirect their energy toward flock of emboli that are passing by, having lower average speed. Slowing the velocity of such particles may reduce the possibility of turbulence. Further, reducing rotational speed of embolus reduces the possibility of nucleation for creating vortices. The fins may also absorb the impact energy of larger particles in blood stream and gracefully bring them to stop. Fins may also provide natural barriers and cover over areas where sealing force between the frame and the aortic wall may vary, such as where plaque is present and the wall surface is heavily textured. The number of fins may be increased to increase the number of emboli that are slowed,

TABLE 1

| Feature | Description/Functionality |
| --- | --- |
| Side Tabs | Bonds to the mesh around the two sides of the frame |
| Nose Cone | Secures the mesh to the frame at distal & proximal end |
| Pouch/pocket | Captures large/deflected emboli |
| | Mitigates turbulence, eddy (flow reversal) and localized vortices |
| | Streamlines flow and reduces pressure difference on the two sides of the mesh |
| | Creates an upward force (due to hemodynamic forces of the flow) that may increase frame stiffness (increased natural frequency of the entire assembly) |
| Flow stabilizers | Guides and channels blood flow, preventing flow stagnation, aft stream. Reduces creation of eddy |
| | Adds to the stiffness of the mesh assembly |
| Flow diverters | Directs flow and diverts emboli from distal end to proximal end of the frame |
| | Reduces leakage rate and emboli intrusion into the sealing interface |
| | Prevents flow mixing near sealing interface |
| | Prevents creation of vortices at seating interface |
| Accumulator | Channels large sizes emboli to aft-proximal end, toward the catheter |
| Fins | Slow down larger diameter embolus and redirect their energy toward flock of emboli with lower average speed |

(1)—Stabilizers may be seam, thermal-weld or suture lines that connect the pouch to the main mesh surface. May protrude slightly above the surface, on either side of bond joints.
(2) The accumulator may mitigate or prevent emboli overflow from the pouch during retrieval of the meshed assembly into the catheter.

Such components as characterized in Table-1 may increase the sealing margin of a frame utilized with the filter, mitigate the passing of particles. For instance, such components may stabilize flow, lowering average flow speed (e.g., during a cardiac cycle), reduce creation of vortices that result in flow reversal, disturb creation of turbulent flow, streamline flow stopped or redirected. The length of the fins may be adjusted (e.g., longer) for capturing heavier and larger embolus that do not conform to a flock of particles passing by.

A variety of filter pattern configurations with a pouch, pocket, lip, cape or other component are utilized for capture and filtering of particles, such as for capturing blood laden debris during cardiovascular procedures. Filter mesh pattern configurations may be designed with seams, flaps, tabs, angles, shapes, and a proximal end pouch, pocket, lip or cape.

Figure 12:
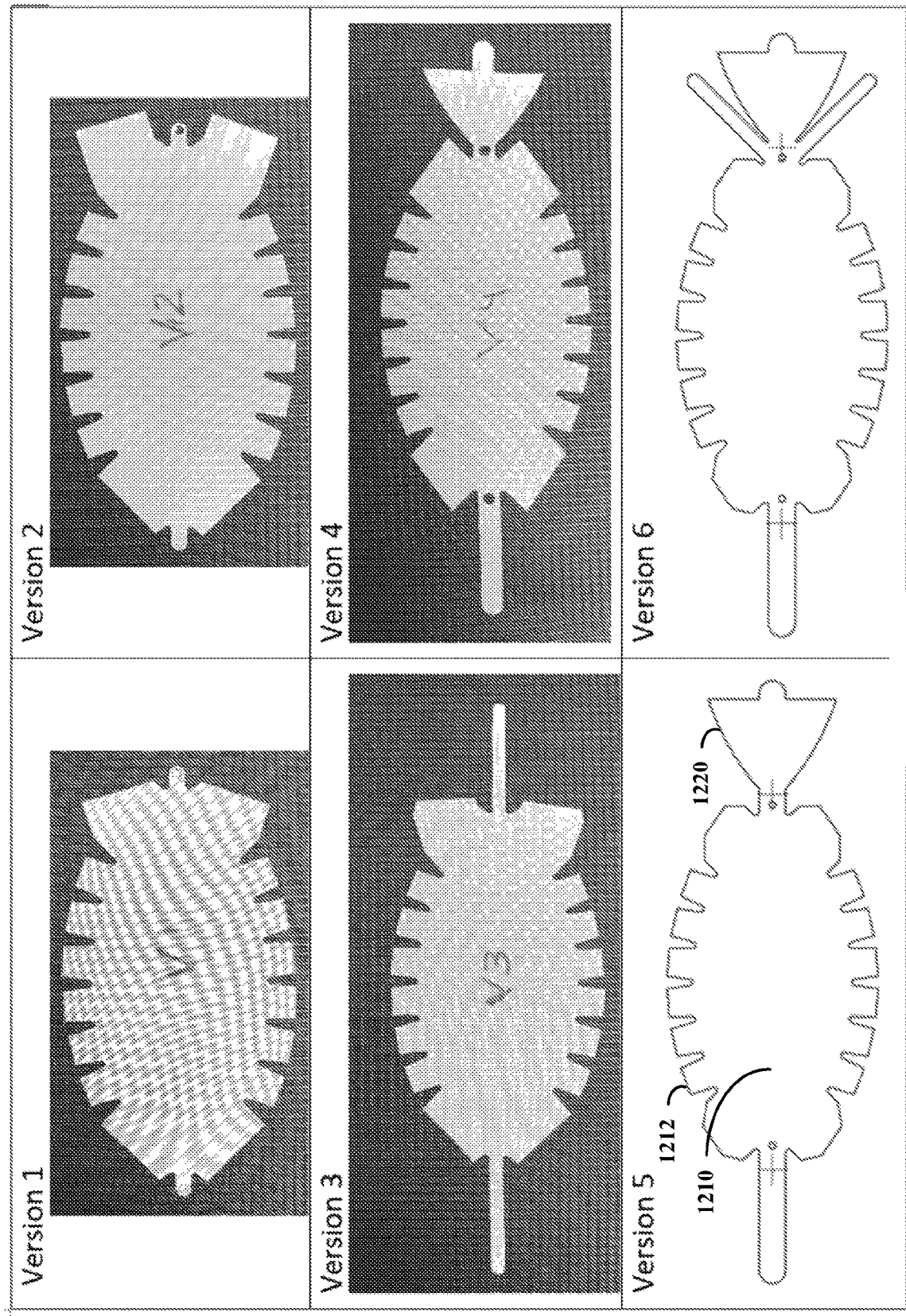
FIG. 12 shows cut filter patterns for filters with pouch-type aspects, as may be implemented with one or more embodiments.
Figure 13:
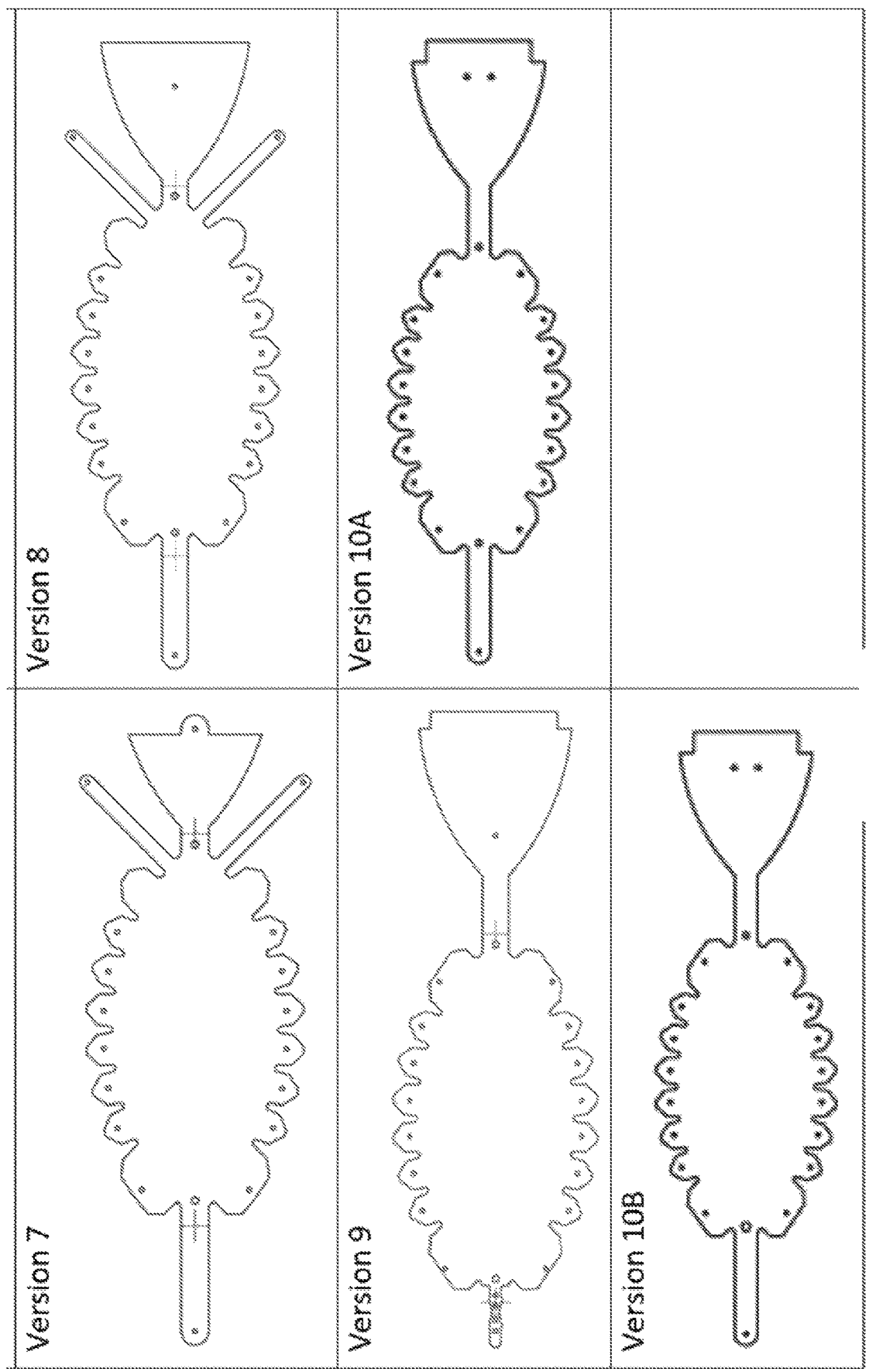
FIG. 13 shows cut filter patterns for filters with pouch-type aspects, as may be implemented with one or more embodiments.

FIGS. 12 and 13 show cut filter patterns for filters with pouch-type aspects, as may be implemented with one or more embodiments. Specifically, FIG. 12 shows versions 1-6, and FIG. 13 shows versions 7-10B. The filters shown may be implemented as or in place of the filters shown in FIGS. 10 and 11, or may be implemented with the frames as shown in FIGS. 1 and 2. Each version depicts tabs that may be folded around a frame for securing the filter to the frame, as well as a trailing portion (right side) that may be secured for forming a pouch as characterized herein. For instance, referring to version 5, a main filter portion 1210 has tabs 1212, and a pouch portion 1220 extends from the right end and may be folded (e.g., along lines as shown) back over the main filter portion to form a pouch, such as depicted in FIG. 10. Further, modifications to the filters may be made to accommodate asymmetrical frames.

Different joining approaches may be used with filters herein, for coupling to frames and, where applicable, to itself. For instance, different welding approaches may be combined for different effects of a filter mesh, different shaping of the a pouch/pocket, and others. For instance, ultrasonic welding may be used to connect a seam down a center of a pouch so that the seam is flat and will round out smoothly, and stitches may be used for the side tabs where the mesh folds over a frame. A stitch may be used at the top and bottom of the mesh covering to make sure it is closed tightly around the frame (a small tail may be left at both top and bottom).

In particular embodiments, a filter apparatus mitigates or prevents embolus from traveling into the great vessels (Brachiocephalic/Innominate, Left Common Carotid, and Left Subclavian arteries), and may be implemented during surgery from the aortic arch, which is the portion of the main artery that bends between the ascending and descending aorta. The aortic arch leaves the heart and ascends, then descends back to create the arch. The aorta distributes blood from the left ventricle of the heart to the rest of the body, and exhibits variable flow characteristics, with hemodynamics of the aortic arch region often exhibiting a non-uniform distribution of pressure and velocity. Particles such as embolus can be filtered under such conditions, using a filter component that conforms to the variable geometry of the aortic arch during cyclic pressure variations, functioning as a filtering umbrella. The collected emboli is extracted and removed through a delivery tube to outside of the body, such as by collapsing and drawing the filter component into a sheath.

In a particular embodiment, a filter mechanism as noted above includes a main frame assembly (FA) and a mesh umbrella, attached securely to the frame. The frame and mesh may be integrated as a single piece/component or with two or more pieces/components. The FA operates to provide a mechanical seal about an opening in an inner wall of vascular tissue with the FA conformed to the wall. Accordingly, micro-emboli and other particulates can be prevented from entering the opening while allowing unrestricted blood flow within the vascular tissue to which the FA is conformed. In various implementations, the FA is operable to maintain the conformity and mechanical seal under variations in cyclic blood pressure for humans under various conditions including those involving surgery, and for various anatomies and conditions such as those involving variations in aortic arch diameter and/or size or the accumulation of plaque. For instance, a mesh may be deployed with an area that is at least twice as large as any opening or openings to be covered. As such, various aspects of the FA may be implemented to facilitate such capture during surgery via catheter deployment, with FA being operable to collapse/trap particulates such as micro-emboli and withdraw the particulates into the catheter for removal upon completion of the surgery. Moreover, by controlling pressure via mechanical spring force, the application of too much pressure can be avoided, as may be useful for instances in which vessel wall stiffening or aneurism may be present.

According to another example embodiment, an apparatus includes a catheter extending from a proximal end to a distal end, a shaft within and operable to move in the catheter, and a filter component connected to an end of the shaft and operable to extend from and retract within the distal end of the catheter. The filter component includes a mesh and inner and outer frames connected by struts, with the mesh is coupled to one or both of the inner frame and the outer frame. The outer frame extends along the inner frame (e.g., in a concentric type arrangement). The struts operate to apply a force between the outer frame and the inner frame, along a direction generally between the frames (tending to push the frames away from one another). The frames may be oval, round or rectangular, with the latter approach facilitating the implementation of a flat surface for applying pressure to tissue. One or more of the mesh, frames and struts can be made of a contiguous material. In various embodiments, the struts apply a force that presses the inner frame and mesh against tissue, such as against an inner region of vascular tissue. Brush-like structures can be used in a perimeter region to facilitate sealing.

As noted herein such approaches can be particularly useful for deploying the mesh against an inner wall of the aortic arch, sealing the mesh around one or more artery openings therein. Deployment may involve, for example, constraining movement of the filter assembly to rotational movement, via the catheter/shaft, which facilitates the application of pressure to the mesh against tissue walls. Further, these approaches can facilitate insertion and filtering while conforming nearly all of the mesh and supporting structure to a sidewall of the aortic arch, allowing blood to flow freely therein while also capturing particles that may otherwise enter the covered artery or arteries. For instance, human red blood cells can be passed while mitigating passage of particles having a dimension larger than the human red blood cells. These particles can be trapped within the mesh/frames such that they can be withdrawn without allowing the particles to further escape back into the bloodstream.

The mesh can be sealed to an interior vessel wall or other tissue in a variety of manners. In some embodiments, the struts operate with the inner frame, outer frame and mesh to, in a deployed state, seal a perimeter region of the mesh to an interior vessel wall by using an applied force to press the mesh perimeter region onto the interior vessel wall. This may involve, for example, applying a force along various struts and between different adjacent regions of the inner and outer frames, such that a distance between the frames varies relative to conformity of one or both frames to tissue anatomy. This flexibility allows the application of sufficient sealing force along the perimeter region, while also accommodating anatomical differences.

In various implementations, the mesh has opposing surfaces and is configured and arranged with the shaft, frames and struts to conform to an inner wall of vascular tissue and cover at least one opening in the vascular tissue. Substantially all of one of the opposing surfaces can be placed in contact with the wall or extending over the at least one opening. This facilitates placement of the mesh predominantly out of the flow of blood in the vascular tissue.

Deployment of the mesh, in these and other contexts, can be effected by the filter component, shaft and catheter by expanding the mesh in a first state in response to the filter component being extended out of the distal end of the catheter, and collapsing the mesh in a second state in response to the filter component being retracted into the catheter. Accordingly, the mesh can be collapsed for fitment into the catheter and expanded upon deployment with a much wider coverage for filtering (e.g., two or many more times the diameter of the catheter).

Forces may be translated the filter component in a variety of manners. In some embodiments, the filter component includes a mechanical spring coupled at the distal end of the shaft. The mechanical spring operates with the shaft and catheter as a base, to apply a spring force that directs the mesh against tissue. For instance, the mechanical spring may operate with the catheter and shaft to apply a spring force to the outer frame in a direction toward the inner frame, with the force being translated from the outer frame to the inner frame via the struts. In some implementations, the spring directly applies a force to the inner frame. The spring may be separate from, or integrated with, a support structure connecting the filter component to the shaft (or as part of the filter component). Such approaches can be used to apply the catheter within a human aortic arch, sealing the mesh to an inner wall of the aortic arch and therein covering at least one opening in the human aortic arch with mesh.

Mesh or other filter material as characterized herein may be implemented in a variety of manners. In some embodiments, a mesh includes a stiffening structure and is operable to fold and unfold in overlapping layers, respectively for retraction into the catheter and for deployment. The stiffening structure may, for example, include additional material on or in the mesh and regions that exhibit lower stiffness for folding. For instance, the mesh may be patterned with differently sized pores and/or with pore density that facilitates longitudinal or lateral folding/stacking behavior. A spiral pattern can facilitate certain opening or closing behaviors. Areas with fewer or no pores can be implemented to induce a stiffening moment.

Figure 14:
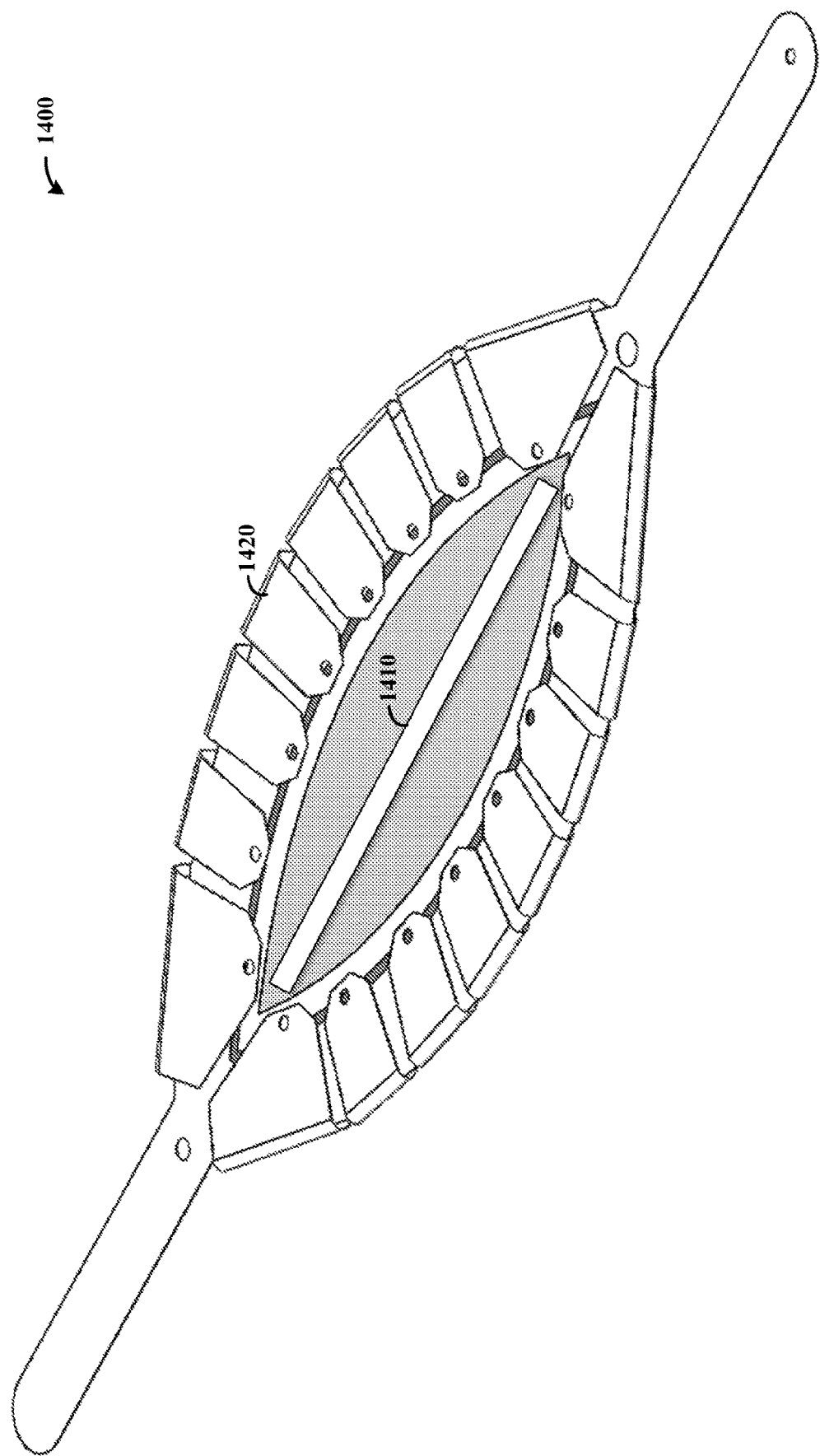
FIG. 14 shows a filter with a sleeve component, in accordance with another embodiment.

FIG. 14 shows a filter 1400 with a sleeve component 1410, in accordance with another embodiment. The sleeve component 1410 is cylindrical and provides constraint of a secondary member, such as a shaft, which may be extended through the sleeve. The sleeve is configured to minimize interference of such secondary members with other devices such as a guidewire, pigtail, or TAVR device that is deployed in a common vessel. The filter 1400 is depicted with a filtering mesh 1420 having flaps that extend over a perimeter frame, however the sleeve 1410 may be implemented with a variety of types of filters, including those shown in the other figures and/or as depicted herein. The sleeve may be made of a solid material, or of a mesh material (e.g., similar to the filter 1420).

FIG. 1 shows an apparatus 100 as may be implemented for supporting a filter or mesh, in accordance with one or more example embodiments. The apparatus 100 includes an inner frame 110 and an outer frame 120 coupled by a struts 130 which operate to apply a force that pushes the inner and outer frame apart. A proximal end 140 is operable for coupling to a shaft, and is coupled to a distal end 150 via the frames. By way of example, the distal end 150 is shown extending at an angle relative to the inner frame 110, which can facilitate placement within a vessel wall (e.g., with the inner frame 110 pressed onto an inner wall within the aortic arch). Such an angle may facilitate placement of the apparatus into the aortic arch with the distal end 150 avoiding intervention into arteries in the walls. In certain implementations, a covering such as a thermoplastic show may be placed over the distal end 150 and facilitate interaction with vascular tissue.

In certain implementations, the proximal end 140 includes a mechanical spring (e.g., which may be integrated within the structure shown), that provides an upward (as depicted) spring force that can also facilitate pressing of the inner frame 110 against an inner wall of a vessel. For instance, with the proximal end 140 coupled to a shaft and inserted into vascular tissue via a catheter, the shaft and proximal end 140 can apply a spring force that tends to push the inner frame 110 upward and against an interior wall of the vascular tissue. Such an approach is particularly useful, for example, within an aortic arch. In some instances, both the frames are pressed against the inner wall of the vascular tissue. With a mesh coupled across the perimeter of the inner frame 110 (and, in some instances, across an overlying perimeter of the outer frame 120), blood flowing through openings in the inner wall within the perimeter of the inner frame is thus filtered via the mesh. Such a mesh may be implemented, for example, with a structure as shown at 160 (partially shown, with such a mesh filling the entire interior area within the perimeter of the inner frame 110). Moreover, a spring force in the proximal end 140 can be used to maintain a seal against a vessel wall under various blood flow conditions and for various anatomies.

In various implementations, mechanical force applied via such a spring and/or the struts 130 may be implemented as a primary force that conforms the structure against the inner wall (e.g., with a mechanical force that is many times larger than fluidic force of blood passing through a vessel). This force may be tuned, for example, during a manufacturing process to tailor the application to a particular use. For instance, the force can be scaled based on a patient's age and condition of the wall against which the mesh is to be deployed, such as may relate to size or the presence of plaque. Controlling an adherence force can facilitate optimization of the size of the mesh, such that the mesh need not be oversized to compensate for any such force.

The apparatus 100 may be made of one or more components. In some embodiments, the inner frame 110, outer frame 120 and struts 130 are formed of a contiguous material, eliminating any need for joints. In various implementations, a mesh (e.g., 160) coupled across the inner frame 110 is also formed with at least the inner frame of a contiguous material. For example, a contiguous nitinol material may be used to form one or all of the components in the apparatus 100. In some embodiments, a thin thermoplastic material is used a mesh and coupled to the inner frame. Where two components are used, they may be joined together using joining methods involving one or more of heat and pressure, adhesive, and lasers. The frames and struts can also be made using polymeric material and/or metallic material. The mesh can be attached directly to the frames and/or to itself.

In various embodiments, a mesh such as mesh 160 includes brush like teeth and grooves that enhance the grip of the mesh over rough terrain (e.g., over the surface of the aortic arch). These brush features may be located in the area of the frames. Small features such as microfeatures (relative to the vessel wall structures) receive the spring force and are highly compressible against the vessel, therein sealing against the vessel.

In various implementations, the apparatus 100 is operable to keep tissue under tension (e.g., along and into the interior of vascular tissue) when the inner and outer frames 110/120 are deployed. In this context, enough sealing pressure is applied to maintain the structure sealed against the wall under conditions in which blood is flowing past and through the mesh. This involves providing a smooth surface of interaction along an interface between the apparatus and the surface of the tissue (e.g., of the aortic arch). Such an approach can be implemented with few or no bumps or raised sections due to welding, bonding, overlap, and reducing/minimizing features such as "gutters," thus facilitating a tight seal with the vascular tissue.

FIG. 2 shows an apparatus 200, in accordance with one or more example embodiments of the present disclosure. The apparatus 200 includes a filter component 210, which may be implemented with inner and outer frames with connecting struts as shown in FIG. 1. The filter component is connected to a shaft 220 that extends through a catheter 230 (e.g., with the shaft and catheter being many times longer than the portions shown). A proximal end 240 of the filter component 210 is secured to the shaft 220 and provides a spring force an in upward direction as depicted in the figure, sealing a perimeter of the filter component 210 against a vessel wall when deployed therein.

FIGS. 3A-3D show respective views of an apparatus 300, in accordance with one or more example embodiments of the present disclosure. As shown in FIG. 3A, the apparatus 300 includes a filter component 310 coupled to a shaft 320 within a catheter 330, with the filter component being retractable into the catheter. A mesh may be coupled to and/or integrated with the filter component 310, across respective rails (e.g., as shown in FIG. 1). FIG. 3B shows a cross-sectional view "A-A" from FIG. 3A, with FIG. 3C showing a view of a distal end of the catheter and shaft as coupled to a proximal end 340 of filter component 310. In various implementations, a portion of the proximal end 340 is locked in place onto the shaft 320 such that it does not extend beyond end 350 of the catheter 330. This maintains componentry within the catheter and out of the bloodstream when deployed in vascular tissue. FIG. 3D shows an alternate view of the apparatus 300.

In various implementations, a portion of the proximal end 340 is locked in place onto the shaft 320 such that it does not extend beyond the end of the catheter 330. This maintains componentry within the catheter and out of the bloodstream when deployed in vascular tissue.

FIG. 4 shows an apparatus 400 as may be implemented to support a mesh or filter, in accordance with one or more example embodiments of the present disclosure. The dimensions shown in FIG. 4 are exemplary, as may be implemented for certain embodiments. The apparatus 400 includes an inner frame 410, outer frame 420 and struts 430 that push the frames apart. Detail "A" provides an exemplary view of these components. A distal end 440 and proximal end 450 are coupled to the frames as shown.

FIGS. 5A-5C show respective views of an apparatus 500 as may be implemented to support a mesh or filter, in accordance with one or more example embodiments of the present disclosure. The apparatus 500 may be implemented similarly to that shown in FIG. 4. As noted in the detail portion "A" of FIG. 5A, inner (510) and outer (520) frames are connected by struts 530 that push the inner frame away from the outer frame and onto a vessel wall. FIGS. 5B and 5C respectively show side and end views of the apparatus 500.

Figure 6:
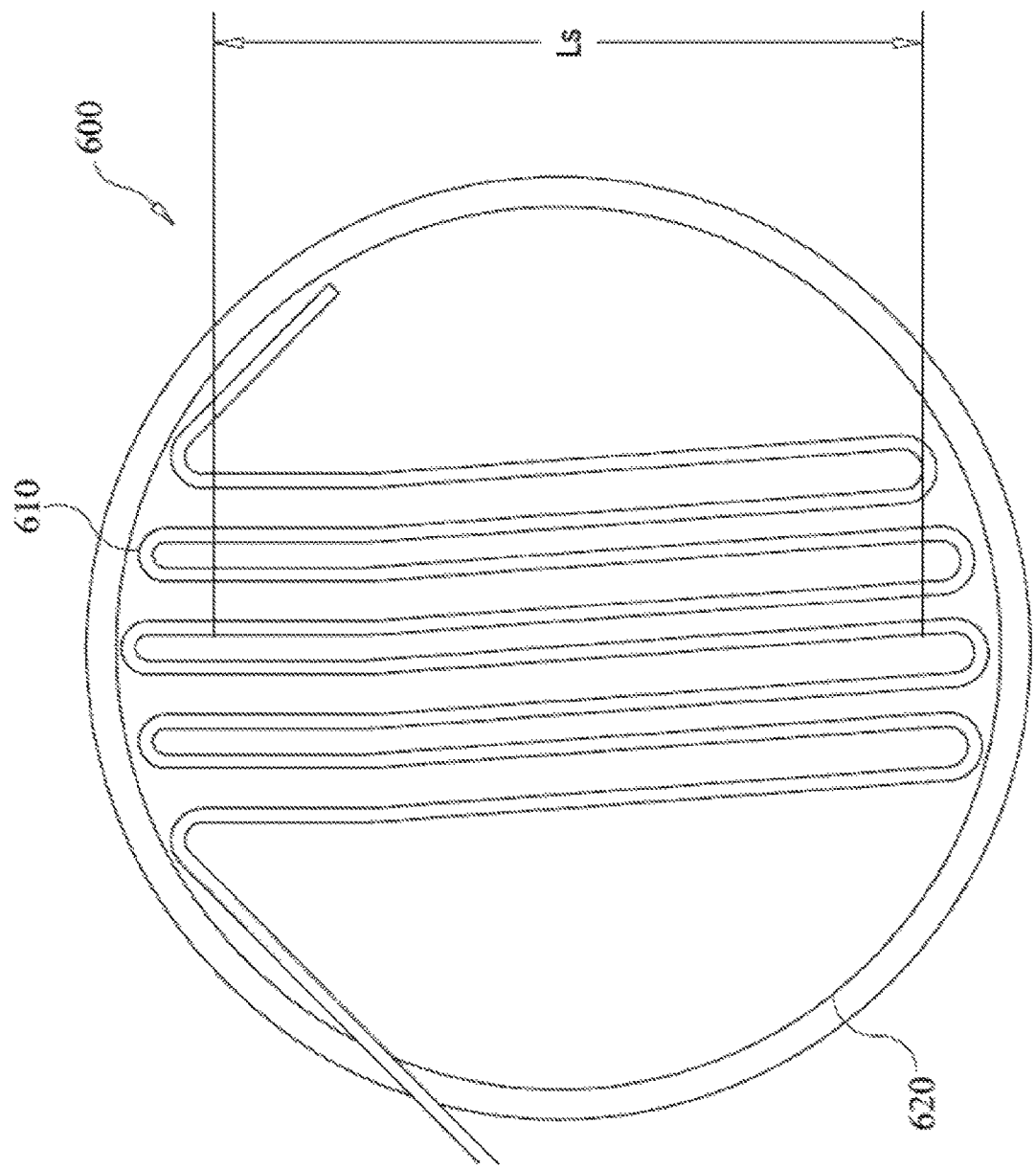
FIG. 6 shows a catheter apparatus with a retracted mesh, in accordance with one or more example embodiments of the present disclosure.

FIG. 6 shows a catheter apparatus 600 with a retracted mesh 610 within a sheath 620, in accordance with one or more example embodiments of the present disclosure. The mesh 610 may, for example, be implemented with filter components as shown in FIGS. 1 and 2, and operable for folding and retraction into a catheter. For instance, after deployment upon a an inner wall of the aortic arch and use for filtering particulates from blood flowing into arteries sealed by the mesh 610, the mesh can be folded and retracted into the sheath 620 as shown to trap and remove the particulates. In various implementations, the mesh 610 has stiffening/ribs structure which enables it to fold and unfold in certain desired direction when it is deployed or retracted within the sheath 620.

Figure 7A:
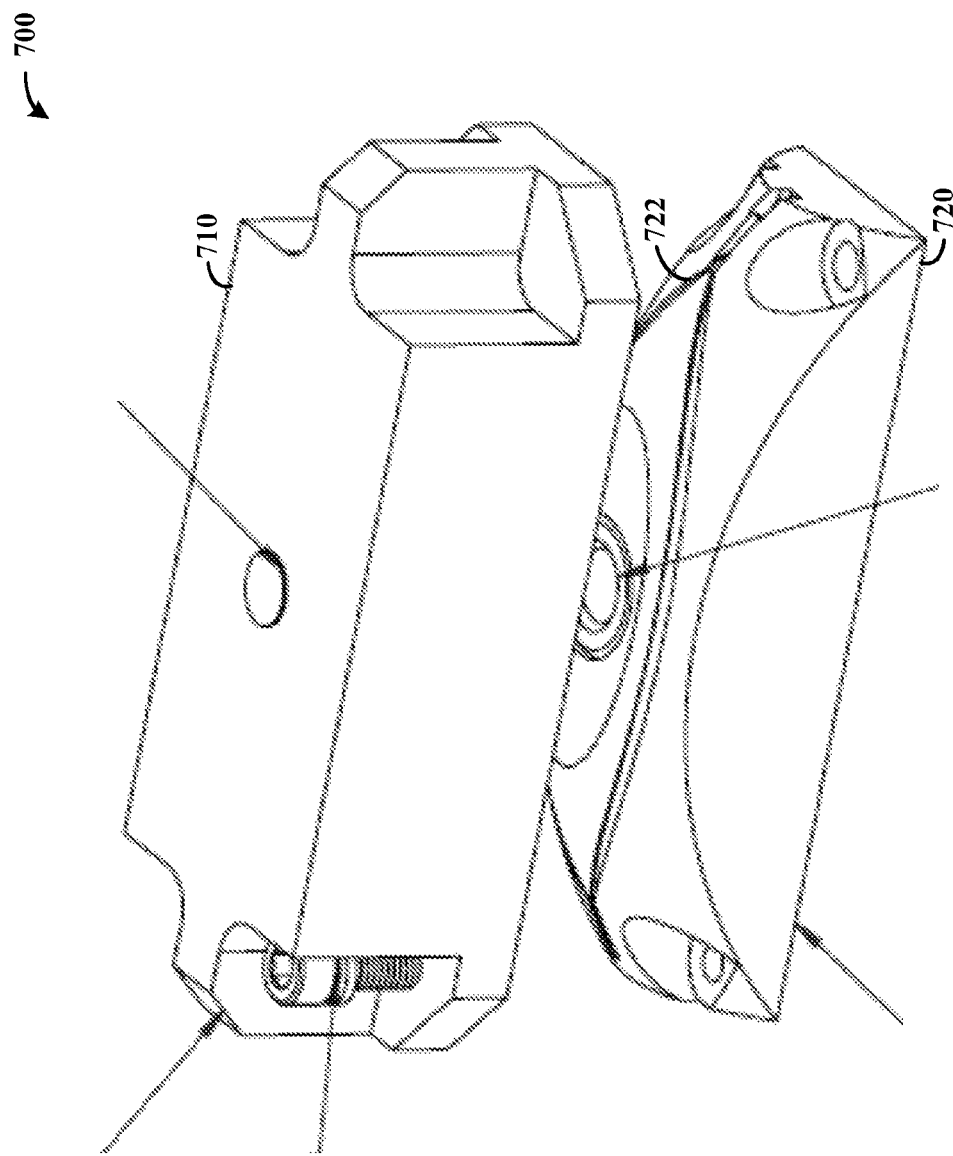

FIGS. 7A-7G show respective views of a filter support manufacturing apparatus 700, as may be implemented in accordance with one or more example embodiments of the present disclosure. The respective dimensions shown are exemplary, with the understanding that the apparatus 700 may be built to a variety of dimensions. The apparatus 700 may be used, for example, to manufacture one or more filter components as shown in other figures herein. Referring to FIG. 7A, an upper fixture 710 and lower fixture 720 are shown in perspective view, with a formed region 722 shown on the lower fixture and operable for forming a filter component.

FIGS. 7B and 7C respectively show end and top views of the apparatus 700, with the upper and lower fixtures 710 and 720 positioned in a forming stage. Section A-A from FIG. 7B is also shown with a region 730 providing a space between the upper and lower fixtures 710/720 for forming the filter component. Such an approach can be facilitated for a variety of molding approaches.

FIG. 7D and FIG. 7E respectively show top and perspective views of the lower fixture 720. As part of FIG. 7D, sections A-A, B-B, D-D and detail C are shown for various cross sections and related detail. Region 730 is recessed for forming part of a filter component.

FIG. 7F and FIG. 7G respectively show top and perspective views of the upper fixture 710. As part of FIG. 7F, sections A-A and B-B are shown for respective cross sections. Region 740 is recessed for forming part of a filter component.

Various other approaches to manufacturing may be implemented to suit particular embodiments. In some embodiments, a starting material is processed to generate a mesh. For example, in some instances a flat nitinol material is used, in which a mesh area is first reduced to less than 0.005" (or less than 0.001") using electro-discharge machining (EDM) or other technique. The frame assembly and mesh patterns are then cut using for example a laser. In some instances, the order of process is reversed such that a frame assembly (frames) are laser cut followed by EDM and laser patterning.

In various embodiments, a frame assembly such as may be implemented with the frame/mesh supporting components shown in one or more of FIGS. 1-5C has a rectangular cross section that provides directional stiffness and also higher force relative to a circular cross section. The rectangular cross section provides a desirable surface contact area and more distributive force, which facilitates sealing. The flat and rectangular frame structure can be implemented with a double frame and struts to keep tissue under tension (no sagging) in both lateral and axial directions. This can facilitate uniform fluid pressure on the mesh and artery openings in the tissue.

Figure 8:
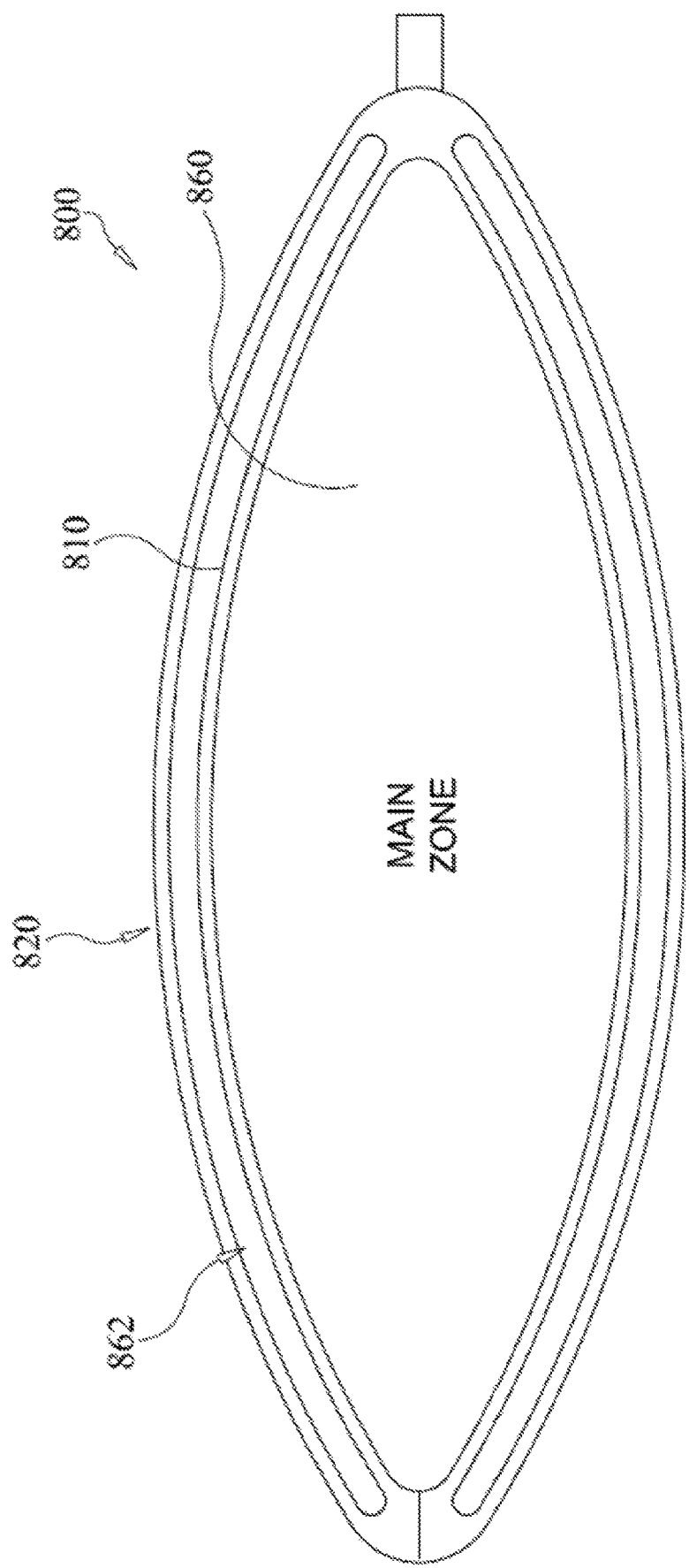
FIG. 8 shows a filter component, as may be implemented with various embodiments.

Referring to FIG. 8, an apparatus 800 is shown, as may be implemented with various embodiments involving filtering. The apparatus 800 includes inner and outer frames 810 and 820, and a mesh 860 that covers a main zone within a perimeter defined by the inner frame and in a region 862 between the inner and outer frames. In various embodiments, two mesh layers are implemented, with a first mesh having a perimeter that aligns with the perimeter of the inner frame 810 a second mesh overlying the first mesh and having a perimeter that aligns with the perimeter of the outer frame 820. In various embodiments, the inner frame 810 and outer frame 820 are operable for pressing against the inner wall of vascular tissue, forming a flat or double seal for filtering blood flowing through an artery in the inner wall. The apparatus 800 may also be implemented with struts between the inner and outer frame, such as shown in FIG. 4.

In various embodiments, a frame assembly is designed to provide spring constant(s) of frame assembly with double flat seal around the main zone. This can increase the reliability of the sealing, provide increased contact force to interior walls of tissue (e.g., aorta) and more adhesion/bonding force between the tissue and the layers. The frame structure may be implemented with spring componentry that facilitates deployment and collapse of the mesh. The frame assembly may be made of four layers to support forces for sealing, deployment, lateral, twisting, pull-in, and constraint. These aspects may be implemented, for example, with the apparatus 800 in FIG. 8 as well as other filter componentry as shown in the other figures.

Figure 9:
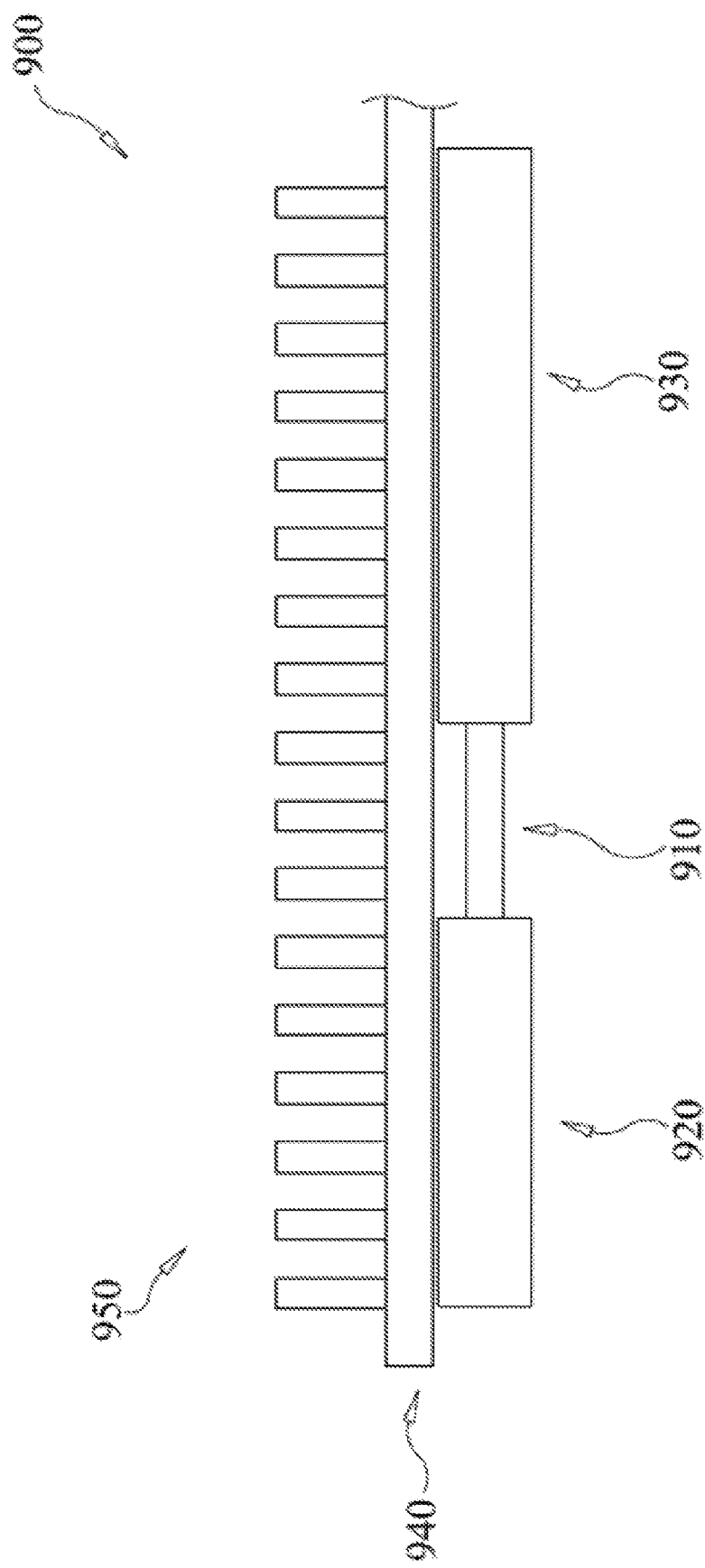
FIG. 9 shows brush features of an apparatus as may be implemented with one or more embodiments.

FIG. 9 shows brush features of an apparatus 900 as may be implemented with one or more embodiments. For instance, the features shown in FIG. 9 may be implemented with the mesh 160 in FIG. 1. The apparatus 900 includes inner and outer frames 910 and 920, coupled by struts 930 that tend to push the frames away from one another. A mesh 940 (a portion shown) is coupled to the frames and brush-like features 950 are coupled to the mesh near the frames. The frames 910 and 920 together with the struts 930 apply pressure to the mesh 940 and to the brush-like features 950 in an upward direction as depicted in the figure, such as for sealing the mesh to an inner wall of vascular tissue (e.g., over an surface of the aortic arch). The brush-like features 950, which may be formed of a common material with the mesh 940, are compressible for facilitating sealing of the mesh against an inner wall.

Based upon the above discussion and illustrations, those skilled in the art will readily recognize that various modifications and changes may be made to the various embodiments without strictly following the exemplary embodiments and applications illustrated and described herein. For example, different types of materials may be used for the various components herein, and other manners in which to expand/collapse mesh-type structures with similar effect can be implemented. Additional and/or differently shaped frame portions or struts may be used to tailor the application to particular anatomies. In addition, the various methods described herein may be implemented with different types of arteries, valves and tissue, as well as different types of live beings. Such modifications do not depart from the true spirit and scope of various aspects of the invention, including aspects set forth in the claims.

What is claimed is:

1. An apparatus comprising:
a first filter having a first perimeter;
a shaft;
a frame coupled to an end of the shaft and to the first filter and having opposing rails connecting proximal and distal ends of the frame, the frame and shaft being configured and arranged to seal the entire first perimeter around an opening in a sidewall of a tubular structure that extends longitudinally along a length, by pressing the frame against the first perimeter and the sidewall; and
a second filter having a second perimeter, with a first portion of the second perimeter coupled to portions of the opposing rails of the frame to which the first perimeter is coupled and with a remaining portion of the second perimeter extending from one of the opposing rails to the other one of the opposing rails and away from the first filter, the second filter being configured and arranged with the first filter and the frame to:
extend into a cross section of the tubular structure away from the frame and the sidewall and form a pouch bound by the second filter and a surface area of the first filter that extends from one of the opposing rails to the other one of the opposing rails, with the frame sealing the first filter around the opening, and
filter particles from a fluid in the tubular structure flowing past the opening and along the length of the sidewall.

2. The apparatus of claim 1, wherein the first and second filters are connected to one another along the first perimeter, and wherein, with the first perimeter sealed around the opening, the second filter extends over the opening with respective edges of the second filter connected to the first perimeter.

3. The apparatus of claim 1, wherein the second filter and a portion of the first filter form the pouch having a first sidewall that includes the first filter and is bound by a portion of the first perimeter, and a second sidewall that includes the second filter, the second sidewall being coupled to the first filter at the portion of the first perimeter and being configured to arch into the cross section of the tubular structure.

4. The apparatus of claim 1, wherein the second filter is a sheet having respective edges fastened to the frame, and a further edge configured to extend into the cross section of the tubular structure.

5. The apparatus of claim 1, wherein the second filter is configured and arranged to mitigate eddy current generation in the tubular structure.

6. The apparatus of claim 5, wherein the second filter is configured and arranged to generate laminar flow by interacting with the fluid flowing in the tubular structure along a surface of the second filter when the fluid is turbulent.

7. The apparatus of claim 1, wherein the second filter is configured to interact with the fluid flowing in the tubular structure to effect one or more of: react to flow variation in the tubular structure; reduce high angles of attack of particulates flowing in the tubular structure relative to the first filter; mitigate pressure gradients in the fluid flowing in the tubular structure; mitigate turbulence; mitigate eddy current; and mitigate vortices.

8. The apparatus of claim 1, wherein the second filter includes a part of the first filter, the first perimeter is connected to the opposing rails on a perimeter of the frame, and edges of the second filter coupled to the opposing rails to form the pouch with the first filter and extending across the opposing rails.

9. The apparatus of claim 1, wherein the second filter is configured and arranged to, in response to momentum of the fluid flowing in the tubular structure, create a reverse moment.

10. The apparatus of claim 9, wherein the second filter is configured to mitigate downstream wake in fluid by using the fluid flowing in the tubular structure to apply a force that reduces curvature of the frame.

11. The apparatus of claim 1, wherein the second filter is configured to use the fluid flowing in the tubular structure to push the frame with a force toward the sidewall.

12. The apparatus of claim 1, further including a flow diverter at the first perimeter, the flow diverter being configured to redirect flow of the fluid in the tubular structure.

13. The apparatus of claim 1, wherein the first and second filters are a continuous mesh sheet and are configured with the frame to provide, when coupled to the frame:
 a proximal end at the proximal end of the frame connected to a distal end of the shaft; and
 a distal end connected to the distal end of the frame at which the apparatus terminates.

14. The apparatus of claim 1, wherein the proximal end of the frame is connected to the shaft, the distal end of the frame extends away from the shaft, and the opposing rails respectively connecting the proximal end of the frame to the distal end of the frame.

15. The apparatus of claim 14, wherein the opposing rails have different shapes and a common length.

16. The apparatus of claim 15, wherein the second filter is configured to move with the opposing rails as they are deployed in the different shapes.

17. The apparatus of claim 14, further including one or more struts connected to a portion of the frame and configured to enhance stiffness of the portion of the frame to which they are connected.

18. The apparatus of claim 1, wherein the opposing rails include pairs of rails extending along the first perimeter and connected to the proximal and distal ends of the frame, each pair of rails being connected to one another by struts.

19. The apparatus of claim 1, wherein the frame is configured to maintain the seal around the opening while the tubular structure expands and contracts relative to pulsatile flow, by flexing in response to the expansion and contraction.

20. The apparatus of claim 1, wherein the frame is asymmetrical.

21. The apparatus of claim 1, wherein different portions of the frame exhibit different flexural rigidity.

22. The apparatus of claim 1, wherein the frame is configured to deflect laterally relative to the shaft.

23. An apparatus comprising:
 a frame having a proximal end, a distal end, and respective rails extending between the proximal and distal ends and forming a first perimeter of the frame;
 a filter coupled to the first perimeter and including:
  opposing surfaces of a common portion of filter material terminating at the rails, including an inner surface and an outer surface, and
  a pouch portion having a second perimeter including a first portion of the second perimeter defined by edges connected to a portion of the rails near the proximal end at which the common portion of filter material terminates, and including a remaining portion of the second perimeter that extends between the rails and over the inner surface, the pouch portion being configured and arranged with the inner surface to extend away from the inner surface and form a partially enclosed filter bound internally by a portion of the inner surface and the pouch portion; and
 an extension arm terminating at a distal end that is connected to the proximal end of the frame, the extension arm being configured with the frame and filter to apply a force to the frame that seals the outer surface of the filter material around an opening in an interior sidewall of a tubular structure to filter fluid exiting the tubular structure via the opening, with the pouch portion extending into the tubular structure for filtering fluid flowing past the frame in the tubular structure.

* * * * *